United States Patent
Guo et al.

(10) Patent No.: US 8,377,949 B2
(45) Date of Patent: Feb. 19, 2013

(54) QUINAZOLINEDIONE CHYMASE INHIBITORS

(75) Inventors: Xin Guo, Danbury, CT (US); Ho Yin Lo, Bethel, CT (US); Chuk Chui Man, Ridgefield, CT (US); Hidenori Takahashi, LaGrangeville, NY (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 160 days.

(21) Appl. No.: 12/673,103

(22) PCT Filed: Aug. 12, 2008

(86) PCT No.: PCT/US2008/072849
§ 371 (c)(1),
(2), (4) Date: Feb. 11, 2010

(87) PCT Pub. No.: WO2009/023655
PCT Pub. Date: Feb. 19, 2009

(65) Prior Publication Data
US 2012/0122863 A1    May 17, 2012

Related U.S. Application Data

(60) Provisional application No. 60/956,189, filed on Aug. 16, 2007.

(51) Int. Cl.
*A01N 43/54* (2006.01)
*A61K 31/517* (2006.01)
*C07D 491/00* (2006.01)
(52) U.S. Cl. ..................... 514/266.1; 544/278
(58) Field of Classification Search .................. 544/278; 514/266.1
See application file for complete search history.

(56) References Cited

U.S. PATENT DOCUMENTS

| | | | | |
|---|---|---|---|---|
| 5,693,637 | A * | 12/1997 | Klinge et al. | 514/221 |
| 6,774,134 | B2 * | 8/2004 | Yu et al. | 514/312 |
| 6,919,331 | B2 * | 7/2005 | Yu et al. | 514/223.2 |
| 2004/0162311 | A1 | 8/2004 | Tsuchiya et al. | |

FOREIGN PATENT DOCUMENTS

| | | |
|---|---|---|
| EP | 0795548 A1 | 9/1997 |
| WO | 0020412 A1 | 4/2000 |

OTHER PUBLICATIONS

International Search Report for PCT/US2008/072849 mailed Nov. 5, 2008.

* cited by examiner

*Primary Examiner* — Paul V. Ward
(74) *Attorney, Agent, or Firm* — Michael P. Morris; Anthony P. Bottino; Usha R. Patel

(57) ABSTRACT

Disclosed are small molecule inhibitors which are useful in treating various diseases and conditions involving Chymase.

7 Claims, No Drawings

QUINAZOLINEDIONE CHYMASE INHIBITORS

APPLICATION DATA

This application is the national phase entry under 35 U.S.C. §371 of International Application No. PCT/US2008/072849 filed Aug. 12, 2008, which also claims benefit to U.S. Provisional application Ser. No. 60/956,189 filed Aug. 16, 2007.

FIELD OF THE INVENTION

The invention relates to small molecule inhibitors which are useful in treating various diseases and conditions involving Chymase.

BACKGROUND OF THE INVENTION

In cardiac tissue of cardiomyopathic patients, transforming growth factor-β(TGF-β), which has been demonstrated to stimulate cardiac fibrosis in animal models (Kuwahara, et al. Circulation, 2002, 106, 130), is increased (Li et al., Circulation, 1997, 96, 874). In the myocardial fibrotic area, it is known that mast cells are increased in number and may contribute to the development of fibroblast proliferation in cardiac tissues of patients with cardiomyopathy (Patella et al., Circulation, 1998, 97, 971). Chymase is a chymotrypsin-like serine protease contained in the secretory granules of mast cells. Although the precise physiological roles of Chymase have not been completely revealed, Chymase is known to transform angiotensin I to angiotensin II and may contribute to activation of TGF-β, matrix proteases, and cytokines (Taipale et al., J. Biol. Chem., 1995, 270, 4689; Takai et al., Life Sci., 1996, 58, 591; Takai et al., Circulation, 1999, 100, 654). A potent and selective Chymase inhibitor may have potential use as a treatment of chronic heart failure, atherosclerosis, restenosis, and myocardial infarction by inhibiting local production of angiotensin II in the heart and release of TGF-β, two independent mediators of cardiac remodeling. Several small molecule Chymase inhibitors have been reported to be efficacious in the cardiomyopathic hamster model of heart failure (Takai et al. J. Pharmacol. Exp. Ther. 2003, 305, 17), in carotid artery injury by a balloon catheter in dogs (Takai et al. J. Pharmacol. Exp. Ther, 2003, 304, 841), and in the hamster left anterior descending coronary artery ligation model of heart failure (WO 03/018061).

An inhibitor may also have potential use for treatment of mast cell mediated diseases such as dermatitis, asthma, chronic obstructive pulmonary disease (COPD), and pulmonary inflammation, since Chymase is implicated in microvascular leakage, neutrophil accumulation, the stimulation of mucus secretion, and the modulation of cytokines (He et al., Eur. J. Pharmacol., 1998, 352, 91). Indeed, Chymase inhibitors have demonstrated efficacy in animal models of abdominal aortic aneurysm (Tsunemi et al., J. Pharm. Exp. Ther., 2004, 309, 879), angiogenesis (Muramatsu et al., Brit. J. Pharm., 2002, 137, 554), pulmonary fibrosis (Sakaguchi et al., Eur. J. Pharm., 2004, 493, 173), adhesion formation (Okamto et al., Eur. J. Pharm., 2004, 484, 357), scleroderma (Shiota et al., Brit. J. Pharm., 2005, 145, 424), asthma and COPD (Garavilla et al., J. Biol. Chem., 2005, 280, 18001), and atopic dermatitis (Imada et al., Jpn. J. Pharm. 2002, 90, 214).

SUMMARY OF THE INVENTION

It is therefore an object of the invention to provide a small molecule a Chymase inhibitor as defined herein, and pharmaceutical compositions thereof.

It is also an object of the invention to provide methods of using said Chymase inhibitors to treat various diseases and conditions related thereto.

It is a further object of the invention to provide processes of preparing said Chymase inhibitors.

DETAILED DESCRIPTION OF THE INVENTION

In a first generic embodiment, there is provided a compound of the formula (I):

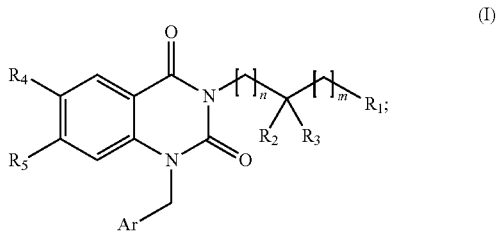

wherein m and n are each independently 0-2;

$R_1$ is halogen, trihalomethyl, cyano, amino, hydroxyl, C1-4 alkyl, C1-4 alkoxyl, $COR_6$, $COOR_6$, $CONR_6R_7$, $NR_6R_7$;

$R_2$ and $R_3$ are each independently hydrogen, halogen, trihalomethyl, cyano, amino, hydroxyl, C1-4 alkyl, carbocycle optionally substituted by halogen or C1-4 alkyl, C1-4 alkoxy, $COR_6$, $COOR_6$, $CONR_6R_7$ or $NR_6R_7$, wherein $R_2$ and $R_3$ cannot simultaneously be hydrogen;

or $R_2$ and $R_3$ optionally together cyclize to the C atom to which they are attached to form a carbocyclic or heterocyclic ring optionally substituted by one or more halogen or C1-4 alkyl, C1-4 alkoxyl, trihalomethyl, cyano, amino, hydroxyl, $COR_6$, $COOR_6$, $CONR_6R_7$ or $NR_6R_7$;

$R_4$ and $R_5$ are each independently hydrogen, halogen, trihalomethyl, cyano, amino, hydroxyl, C1-4 alkyl, C1-4 alkoxyl, $COR_6$, $COOR_6$, $CONR_6R_7$ or $NR_6R_7$;

Ar is a mono- or poly-substituted or unsubstituted fused heteroaromatic group having 7-10 carbon atoms and containing one or more hetero atoms selected from the group consisting of an oxygen atom, a nitrogen atom and a sulfur atom in its ring(s); each substituent on said aromatic or heteroaromatic groups is selected from a halogen, hydroxyl, nitro, cyano, a linear or branched C1-6 alkyl group, a linear or branched C1-6 alkoxy (including the case in which two adjacent groups form an acetal bond), a linear or branched C1-6 alkylthio, a linear or branched C1-6 alkylsulfonyl group, phenylsulfonyl, a linear or branched C1-6 acyl group, a linear or branched C1-6 acylamino, trihalomethyl, trihalomethoxy, phenyl, oxo, $COOR_6$, $CONR_6R_7$, $SO_2NR_6R_7$, NR6R7 and phenoxy group that may be substituted by one or more halogen atoms;

$R_6$, $R_7$ each independently represent a hydrogen atom or linear or branched alkyl group having 1-6 carbon atoms, or $R_6$ and $R_7$ optionally together represent —$CH_2$—$CH_2$—, —$CH_2$—$CH_2$—$CH_2$— or —$CH_2$—$CH_2$—$CH_2$ and cyclize to the N atom to which they are attached to form a heterocycle ring optionally substituted by one or more C1-4 alkyl;

or the pharmaceutically acceptable salts thereof.

In another embodiment, there is provided a compound as described herein above and wherein:

Ar is indolyl, azaindolyl, isoindolyl, benzoxazolyl, benzothiazolyl, benzisothiazolyl, benzimidazolyl, isoquinolinyl, quinolinyl, benzofuranyl, benzodioxolyl or indazolyl each optionally substituted with a group selected from a halogen, hydroxyl, nitro, cyano, a linear or branched C1-6 alkyl group, a linear or branched C1-6 alkoxy (including the case in which two adjacent groups form an acetal bond), a linear or branched C1-6 alkylthio, a linear or branched C1-6 alkylsulfonyl group, phenylsulfonyl, a linear or branched C1-6 acyl group, a linear or branched C1-6 acylamino, trihalomethyl, trihalomethoxy, phenyl, oxo, $COOR_6$, $CONR_6R_7$, $SO_2NR_6R_7$, $NR_6R_7$ and phenoxy group that may be substituted by one or more halogen atoms;

$R_1$ is C1-4 alkoxyl, $COR_6$, $COOR_6$ or $CONR_6R_7$;

$R_2$ and $R_3$ are each independently hydrogen, C1-4 alkyl, C3-6 cycloalkyl or phenyl each ring is optionally substituted by halogen or C1-4 alkyl, wherein $R_2$ and $R_3$ cannot simultaneously be hydrogen;

or $R_2$ and $R_3$ optionally together cyclize to the C atom to which they are attached to form a C3-6 cycloalkyl or C3-6 heterocyclic ring optionally substituted by one or more halogen or C1-4 alkyl;

$R_4$ and $R_5$ are each independently hydrogen, C1-4 alkyl or C1-4 alkoxy.

In another embodiment, there is provide a compound as described hereinabove and wherein:

Ar is indolyl or benzisothiazolyl each optionally substituted with a group selected from a halogen, hydroxyl, nitro, cyano, a linear or branched C1-6 alkyl group, a linear or branched C1-6 alkoxy, a linear or branched C1-6 alkylthio, a linear or branched C1-6 alkylsulfonyl group, a linear or branched C1-6 acyl group, a linear or branched C1-6 acylamino, trihalomethy and trihalomethoxy;

$R_1$ is $COR_6$, $COOR_6$ or $CONR_6R_7$;

$R_2$ and $R_3$ are each independently hydrogen, methyl, ethyl, propyl, butyl, cyclopropyl, cyclohexyl or phenyl each ring is optionally substituted by halogen or C1-4 alkyl, wherein $R_2$ and $R_3$ cannot simultaneously be hydrogen;

or $R_2$ and $R_3$ optionally together cyclize to the C atom to which they are attached to form cyclohexyl, tetrahydropyranyl, optionally substituted by one or more halogen or C1-4 alkyl.

In another embodiment, there is provide a compound as described hereinabove and wherein:

Ar is indolyl or benzisothiazolyl each optionally substituted with a linear or branched C1-6 alkyl group.

In another embodiment, there is provide a compound as described hereinabove and wherein:

Ar is

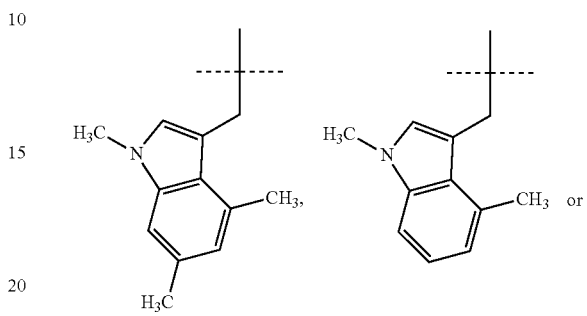

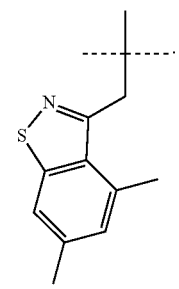

In another embodiment, there is provided compounds of the formula (I) as described in Table I which can be made as described in the schemes and examples herein below, and by methods apparent to those of ordinary skill in the art:

TABLE 1

| Chiral | (S)-2-[1-(1,4-Dimethyl-1H-indol-3-ylmethyl)-2,4-dioxo-1,4-dihydro-2H-quinazolin-3-yl]-pentanoic acid |
|---|---|

TABLE 1-continued
| Structure | | Name |
|---|---|---|
| 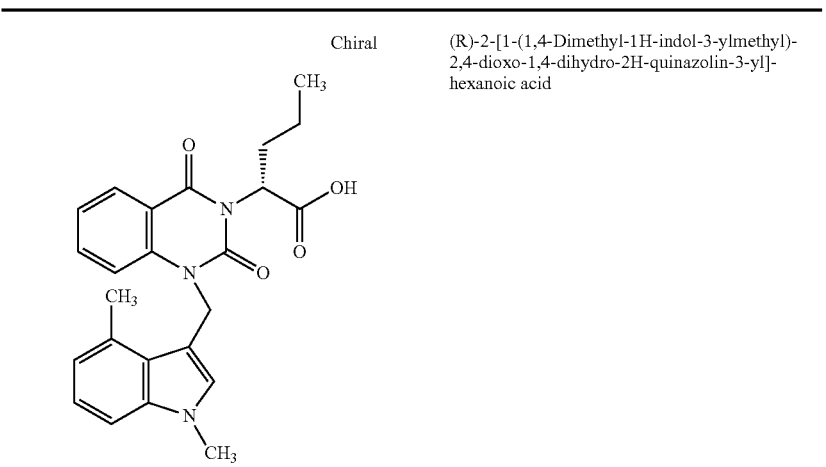 | Chiral | (R)-2-[1-(1,4-Dimethyl-1H-indol-3-ylmethyl)-2,4-dioxo-1,4-dihydro-2H-quinazolin-3-yl]-hexanoic acid |
| 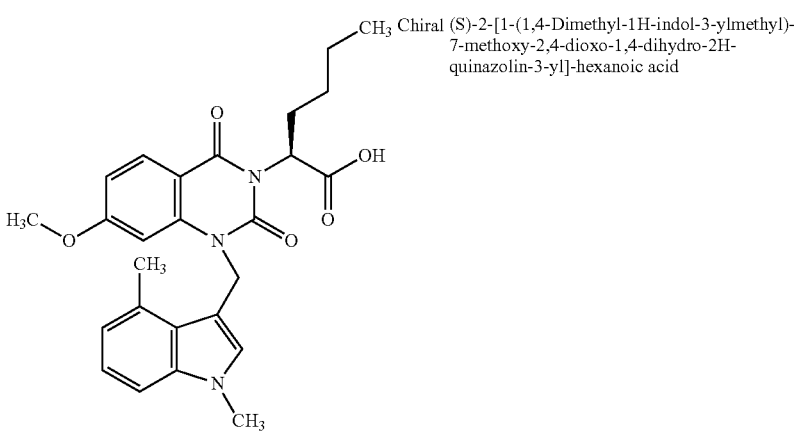 | Chiral | (S)-2-[1-(1,4-Dimethyl-1H-indol-3-ylmethyl)-7-methoxy-2,4-dioxo-1,4-dihydro-2H-quinazolin-3-yl]-hexanoic acid |
| 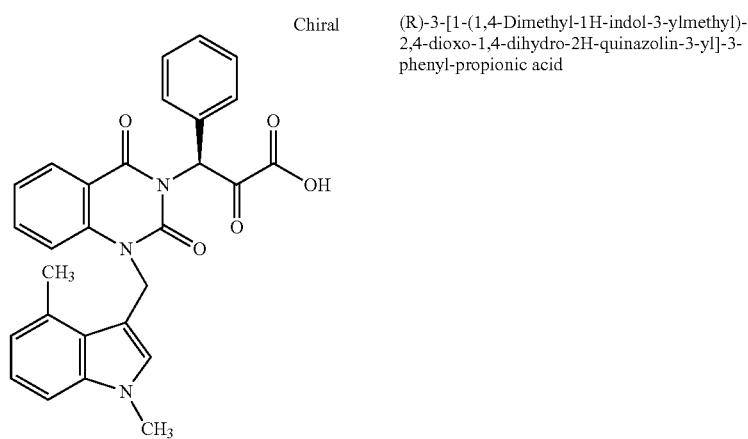 | Chiral | (R)-3-[1-(1,4-Dimethyl-1H-indol-3-ylmethyl)-2,4-dioxo-1,4-dihydro-2H-quinazolin-3-yl]-3-phenyl-propionic acid |

TABLE 1-continued
| | | |
|---|---|---|
| 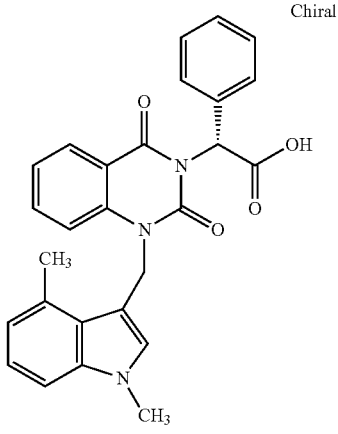 [SMILES: Cc1cccc2c1c(Cn1c(=O)n([C@@H](C(=O)O)c3ccccc3)c(=O)c3ccccc31)cn2C] | Chiral | (R)-[1-(1,4-Dimethyl-1H-indol-3-ylmethyl)-2,4-dioxo-1,4-dihydro-2H-quinazolin-3-yl]-phenyl-acetic acid |
| 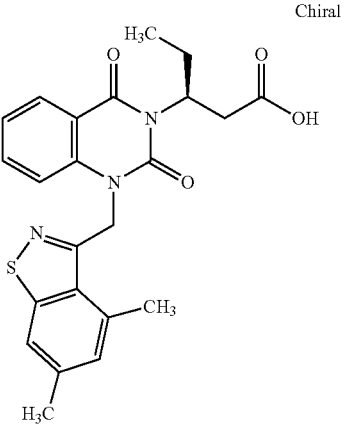 [SMILES: CC[C@@H](CC(=O)O)n1c(=O)c2ccccc2n(Cc2nsc3cc(C)cc(C)c23)c1=O] | Chiral | (S)-3-[1-(4,6-Dimethyl-1,2-benzisothiazol-3-ylmethyl)-2,4-dioxo-1,4-dihydro-2H-quinazolin-3-yl]-pentanoic acid |
| 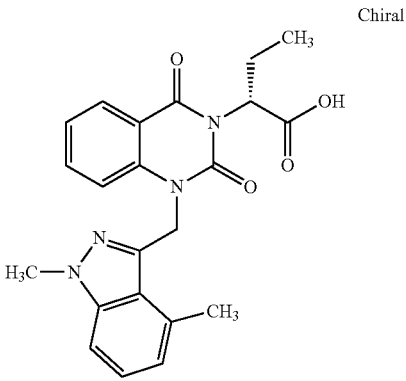 [SMILES: CC[C@H](C(=O)O)n1c(=O)c2ccccc2n(Cc2nn(C)c3cccc(C)c23)c1=O] | Chiral | (R)-2-[1-(1,4-Dimethyl-1H-indol-3-ylmethyl)-2,4-dioxo-1,4-dihydro-2H-quinazolin-3-yl]-butyric acid |

TABLE 1-continued
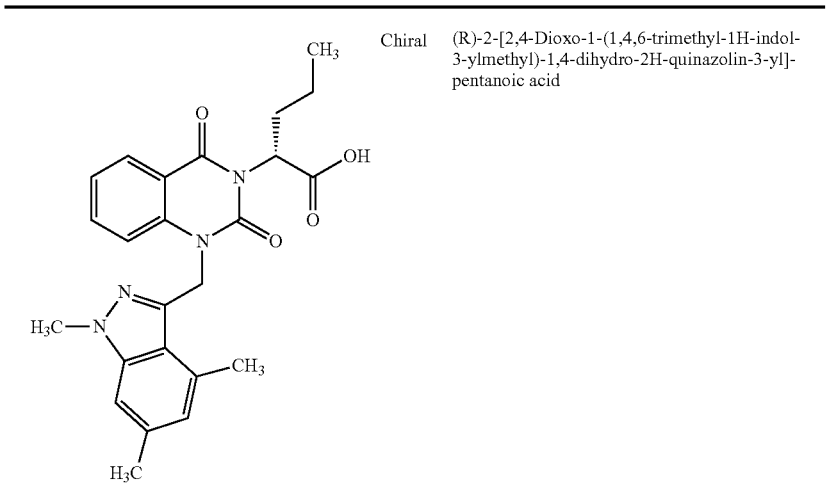
Chiral  (R)-2-[2,4-Dioxo-1-(1,4,6-trimethyl-1H-indol-3-ylmethyl)-1,4-dihydro-2H-quinazolin-3-yl]-pentanoic acid
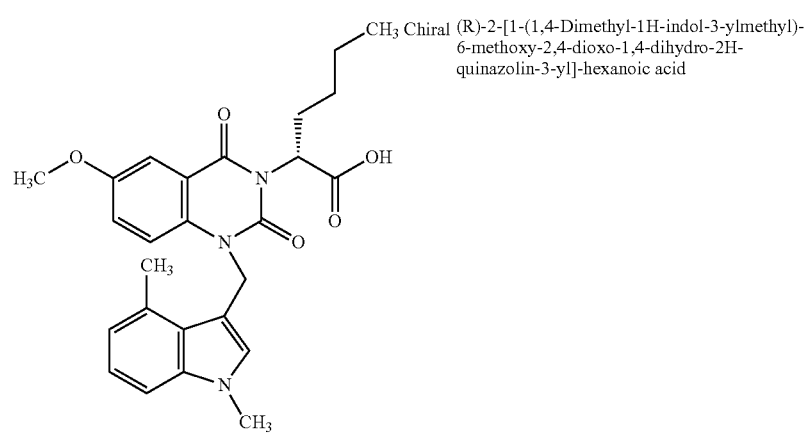
Chiral  (R)-2-[1-(1,4-Dimethyl-1H-indol-3-ylmethyl)-6-methoxy-2,4-dioxo-1,4-dihydro-2H-quinazolin-3-yl]-hexanoic acid
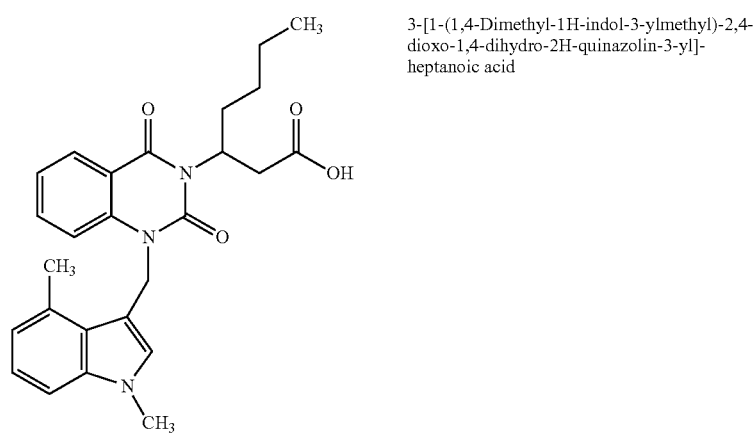
3-[1-(1,4-Dimethyl-1H-indol-3-ylmethyl)-2,4-dioxo-1,4-dihydro-2H-quinazolin-3-yl]-heptanoic acid TABLE 1-continued
| | | |
|---|---|---|
| 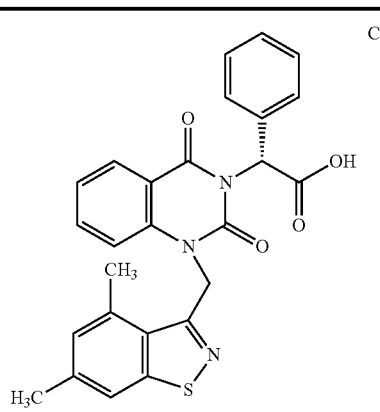 | Chiral | (R)-[1-(4,6-Dimethyl-1,2-benzisothiazol-3-ylmethyl)-2,4-dioxo-1,4-dihydro-2H-quinazolin-3-yl]-phenyl-acetic acid |
| 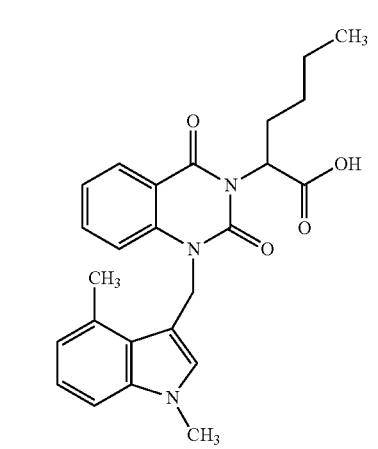 [SMILES: CCCCC(C(=O)O)n1c(=O)c2ccccc2n(Cc2cn(C)c3cccc(C)c23)c1=O] | | 2-[1-(1,4-Dimethyl-1H-indol-3-ylmethyl)-2,4-dioxo-1,4-dihydro-2H-quinazolin-3-yl]-hexanoic acid |
| 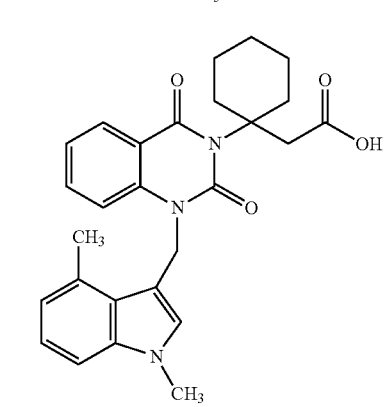 | | {1-[1-(1,4-Dimethyl-1H-indol-3-ylmethyl)-2,4-dioxo-1,4-dihydro-2H-quinazolin-3-yl]-cyclohexyl}-acetic acid |
| 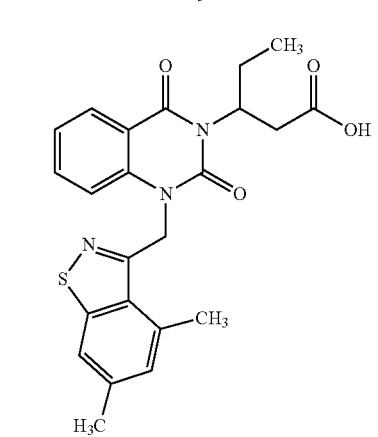 | | 3-[1-(4,6-Dimethyl-1,2-benzisothiazol-3-ylmethyl)-2,4-dioxo-1,4-dihydro-2H-quinazolin-3-yl]-pentanoic acid |

TABLE 1-continued
| Structure | Name |
|---|---|
| 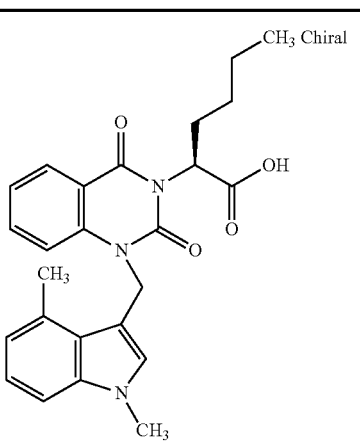 | (S)-2-[1-(1,4-Dimethyl-1H-indol-3-ylmethyl)-2,4-dioxo-1,4-dihydro-2H-quinazolin-3-yl]-hexanoic acid |
| 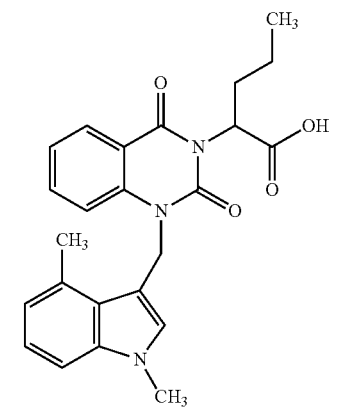 [SMILES: CCCC(C(=O)O)n1c(=O)c2ccccc2n(Cc2cn(C)c3cccc(C)c23)c1=O] | 2-[1-(1,4-Dimethyl-1H-indol-3-ylmethyl)-2,4-dioxo-1,4-dihydro-2H-quinazolin-3-yl]-pentanoic acid |
| 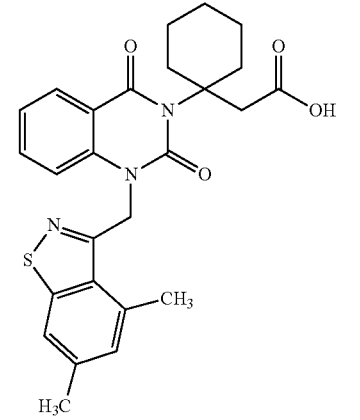 [SMILES: Cc1cc(C)c2c(Cn3c(=O)n(C4(CC(=O)O)CCCCC4)c(=O)c4ccccc43)nsc2c1] | {1-[1-(4,6-Dimethyl-1,2-benzisothiazol-3-ylmethyl)-2,4-dioxo-1,4-dihydro-2H-quinazolin-3-yl]-cyclohexyl}-acetic acid |
| 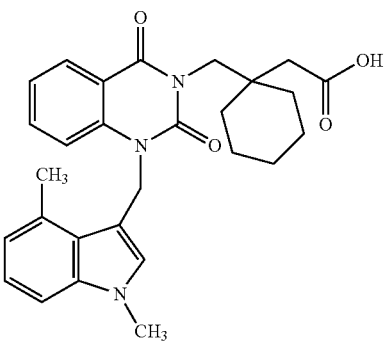 [SMILES: Cc1cccc2c1c(Cn1c(=O)n(CC3(CC(=O)O)CCCCC3)c(=O)c3ccccc31)cn2C] | {1-[1-(1,4-Dimethyl-1H-indol-3-ylmethyl)-2,4-dioxo-1,4-dihydro-2H-quinazolin-3-ylmethyl]-cyclohexyl}-acetic acid |

TABLE 1-continued
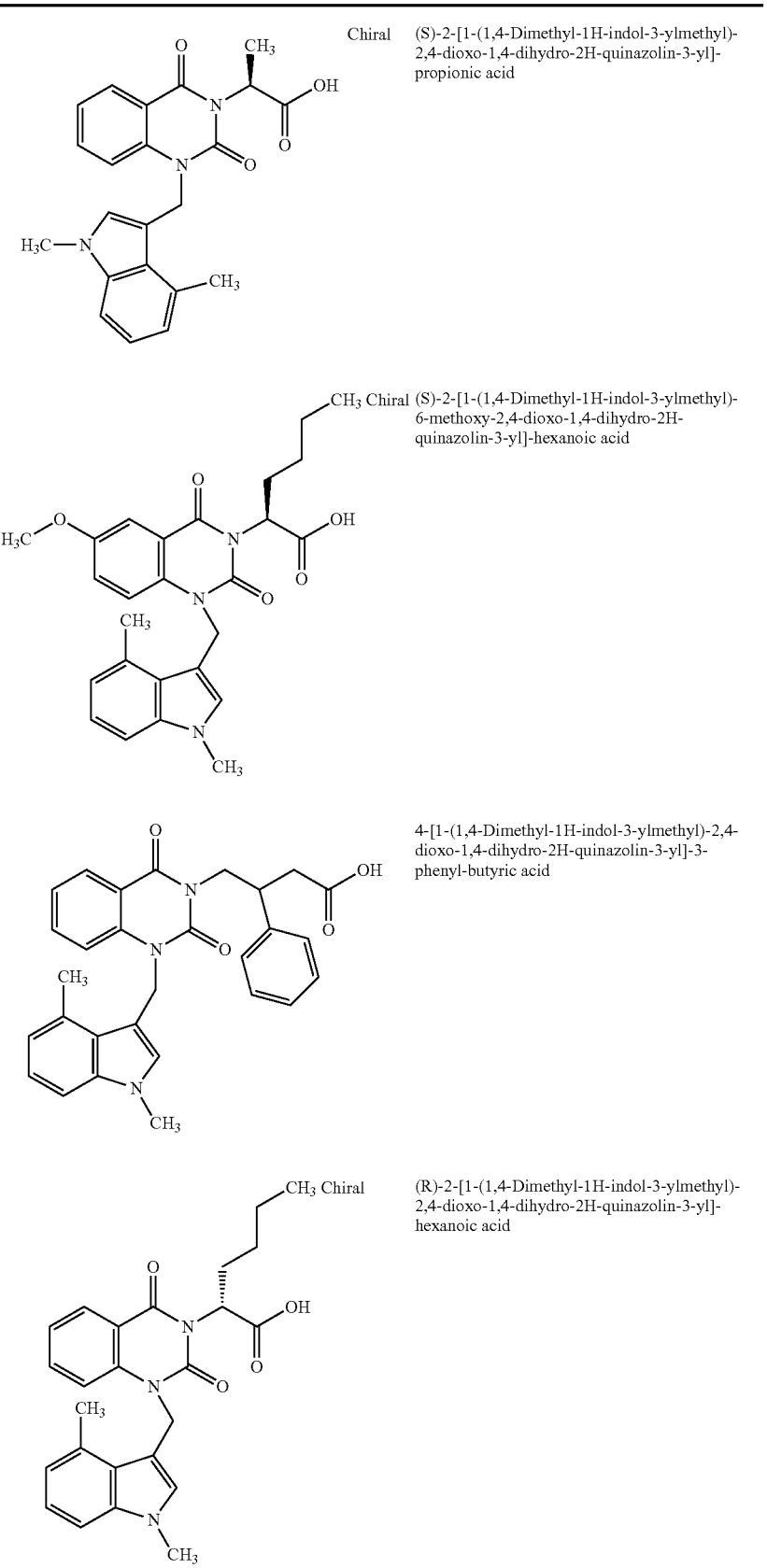
| | |
|---|---|
| Chiral | (S)-2-[1-(1,4-Dimethyl-1H-indol-3-ylmethyl)-2,4-dioxo-1,4-dihydro-2H-quinazolin-3-yl]-propionic acid |
| Chiral | (S)-2-[1-(1,4-Dimethyl-1H-indol-3-ylmethyl)-6-methoxy-2,4-dioxo-1,4-dihydro-2H-quinazolin-3-yl]-hexanoic acid |
| | 4-[1-(1,4-Dimethyl-1H-indol-3-ylmethyl)-2,4-dioxo-1,4-dihydro-2H-quinazolin-3-yl]-3-phenyl-butyric acid |
| Chiral | (R)-2-[1-(1,4-Dimethyl-1H-indol-3-ylmethyl)-2,4-dioxo-1,4-dihydro-2H-quinazolin-3-yl]-hexanoic acid |

TABLE 1-continued
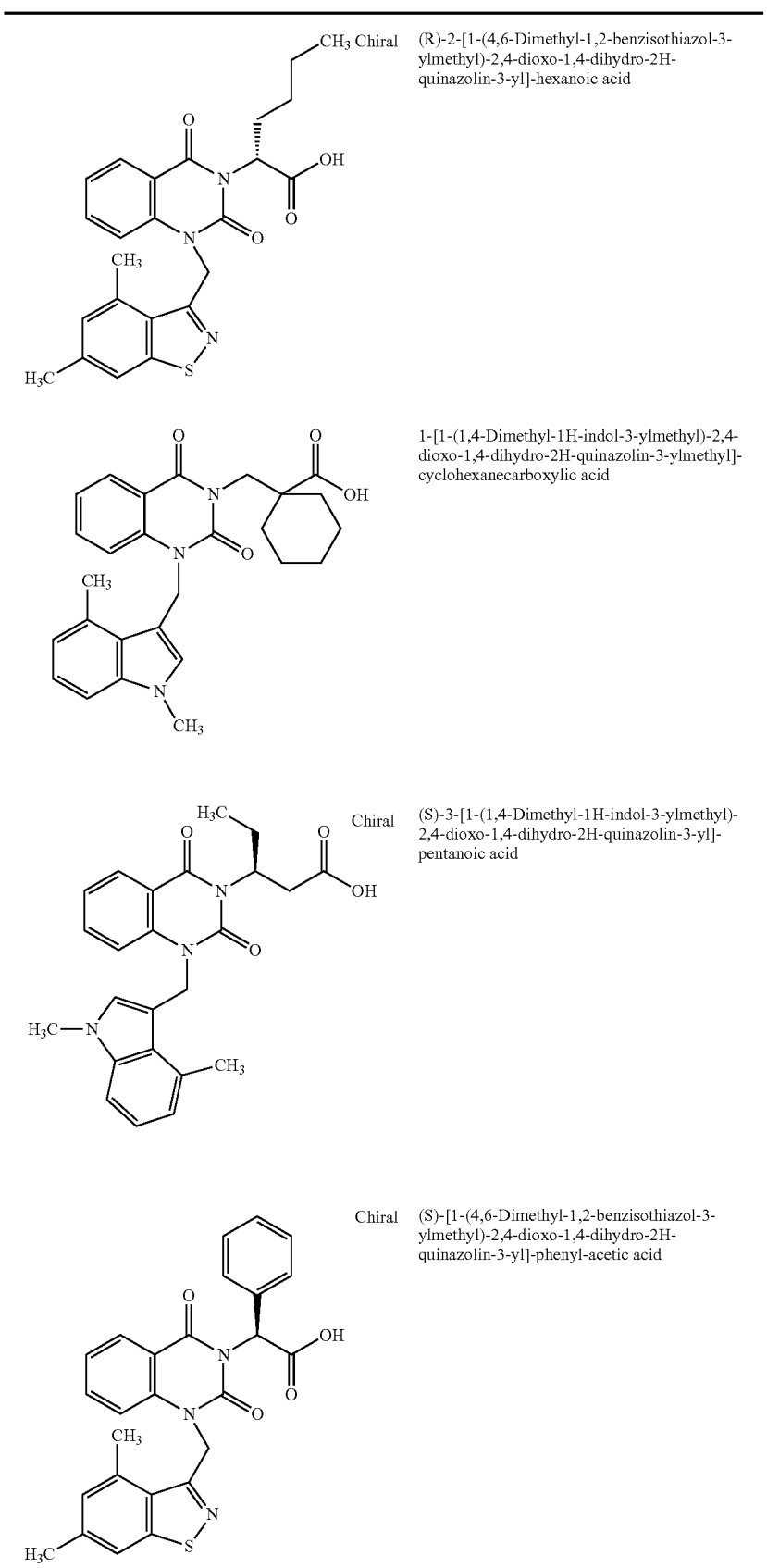
(R)-2-[1-(4,6-Dimethyl-1,2-benzisothiazol-3-ylmethyl)-2,4-dioxo-1,4-dihydro-2H-quinazolin-3-yl]-hexanoic acid
1-[1-(1,4-Dimethyl-1H-indol-3-ylmethyl)-2,4-dioxo-1,4-dihydro-2H-quinazolin-3-ylmethyl]-cyclohexanecarboxylic acid
(S)-3-[1-(1,4-Dimethyl-1H-indol-3-ylmethyl)-2,4-dioxo-1,4-dihydro-2H-quinazolin-3-yl]-pentanoic acid
(S)-[1-(4,6-Dimethyl-1,2-benzisothiazol-3-ylmethyl)-2,4-dioxo-1,4-dihydro-2H-quinazolin-3-yl]-phenyl-acetic acid TABLE 1-continued
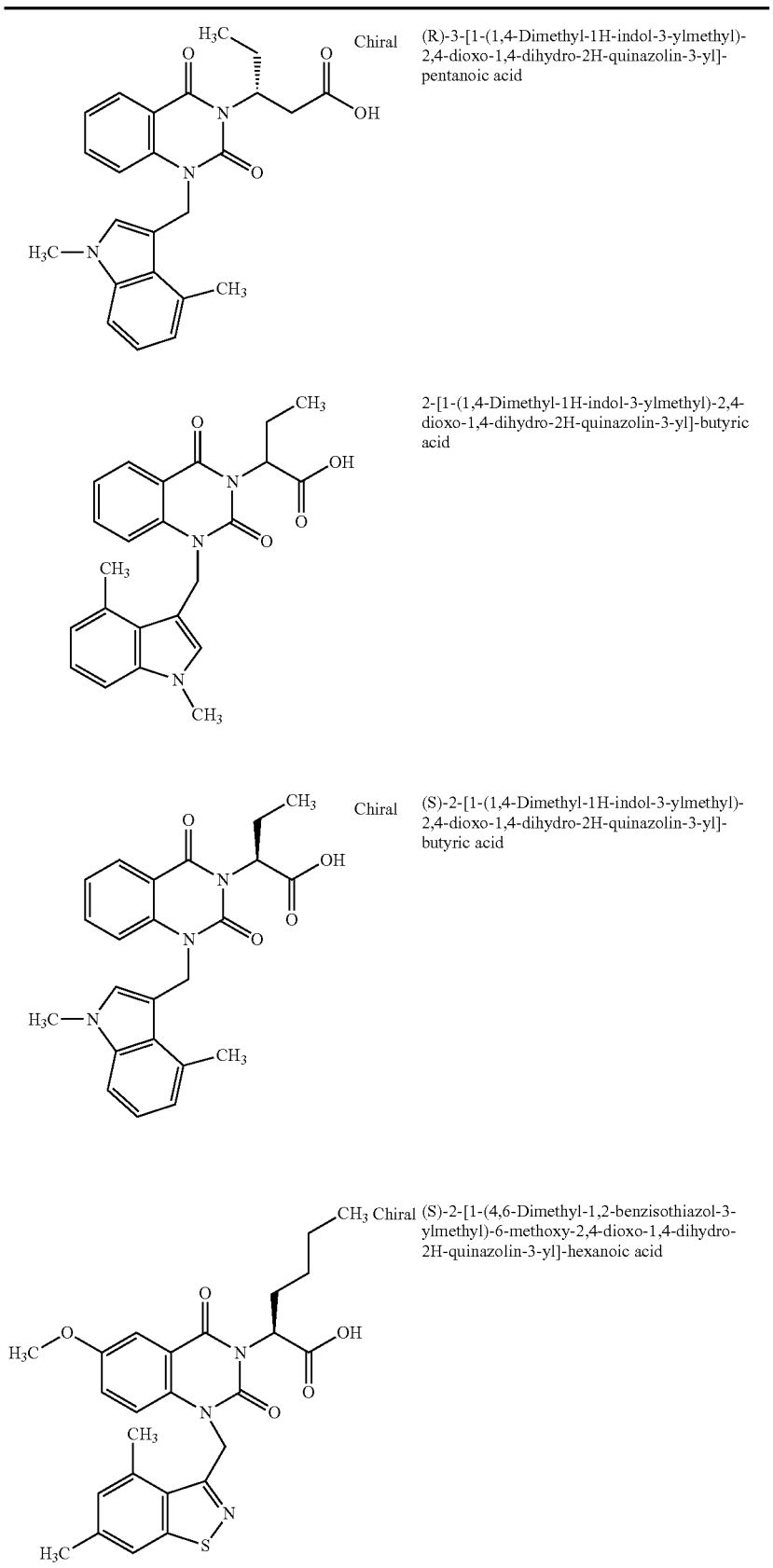
(R)-3-[1-(1,4-Dimethyl-1H-indol-3-ylmethyl)-2,4-dioxo-1,4-dihydro-2H-quinazolin-3-yl]-pentanoic acid
2-[1-(1,4-Dimethyl-1H-indol-3-ylmethyl)-2,4-dioxo-1,4-dihydro-2H-quinazolin-3-yl]-butyric acid
(S)-2-[1-(1,4-Dimethyl-1H-indol-3-ylmethyl)-2,4-dioxo-1,4-dihydro-2H-quinazolin-3-yl]-butyric acid
(S)-2-[1-(4,6-Dimethyl-1,2-benzisothiazol-3-ylmethyl)-6-methoxy-2,4-dioxo-1,4-dihydro-2H-quinazolin-3-yl]-hexanoic acid TABLE 1-continued

| Structure | Chirality | Name |
|---|---|---|
| | Chiral | (R)-2-[1-(1,4-Dimethyl-1H-indol-3-ylmethyl)-2,4-dioxo-1,4-dihydro-2H-quinazolin-3-yl]-propionic acid |
| | Chiral | (S)-[1-(1,4-Dimethyl-1H-indol-3-ylmethyl)-2,4-dioxo-1,4-dihydro-2H-quinazolin-3-yl]-phenyl-acetic acid |
| | | (S)-(4-Chloro-phenyl)-[1-(4,6-dimethyl-1,2-benzisothiazol-3-ylmethyl)-2,4-dioxo-1,4-dihydro-2H-quinazolin-3-yl]-acetic acid |
| | | 3-[1-(1,4-Dimethyl-1H-indol-3-ylmethyl)-2,4-dioxo-1,4-dihydro-2H-quinazolin-3-yl]-pentanoic acid |

TABLE 1-continued

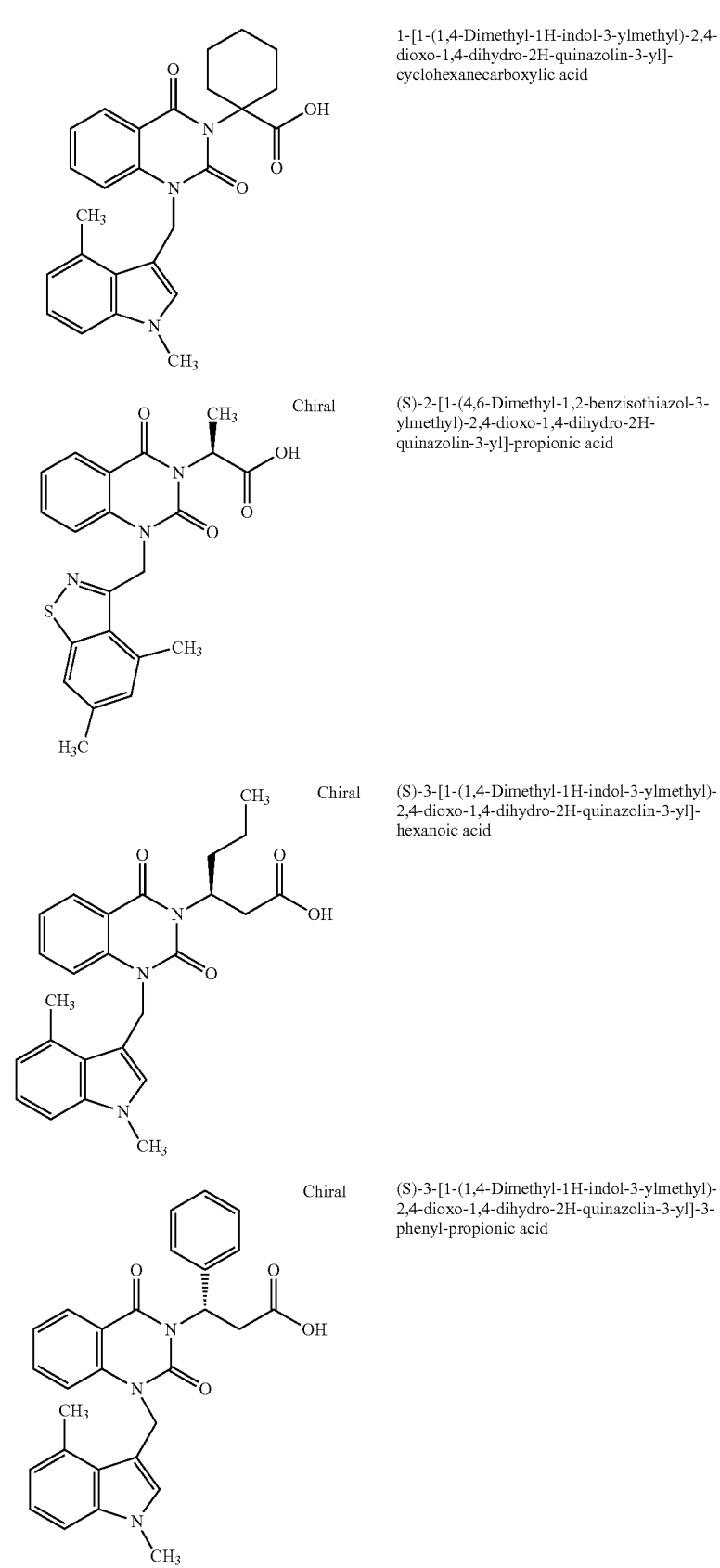

1-[1-(1,4-Dimethyl-1H-indol-3-ylmethyl)-2,4-dioxo-1,4-dihydro-2H-quinazolin-3-yl]-cyclohexanecarboxylic acid Chiral (S)-2-[1-(4,6-Dimethyl-1,2-benzisothiazol-3-ylmethyl)-2,4-dioxo-1,4-dihydro-2H-quinazolin-3-yl]-propionic acid Chiral (S)-3-[1-(1,4-Dimethyl-1H-indol-3-ylmethyl)-2,4-dioxo-1,4-dihydro-2H-quinazolin-3-yl]-hexanoic acid Chiral (S)-3-[1-(1,4-Dimethyl-1H-indol-3-ylmethyl)-2,4-dioxo-1,4-dihydro-2H-quinazolin-3-yl]-3-phenyl-propionic acid TABLE 1-continued

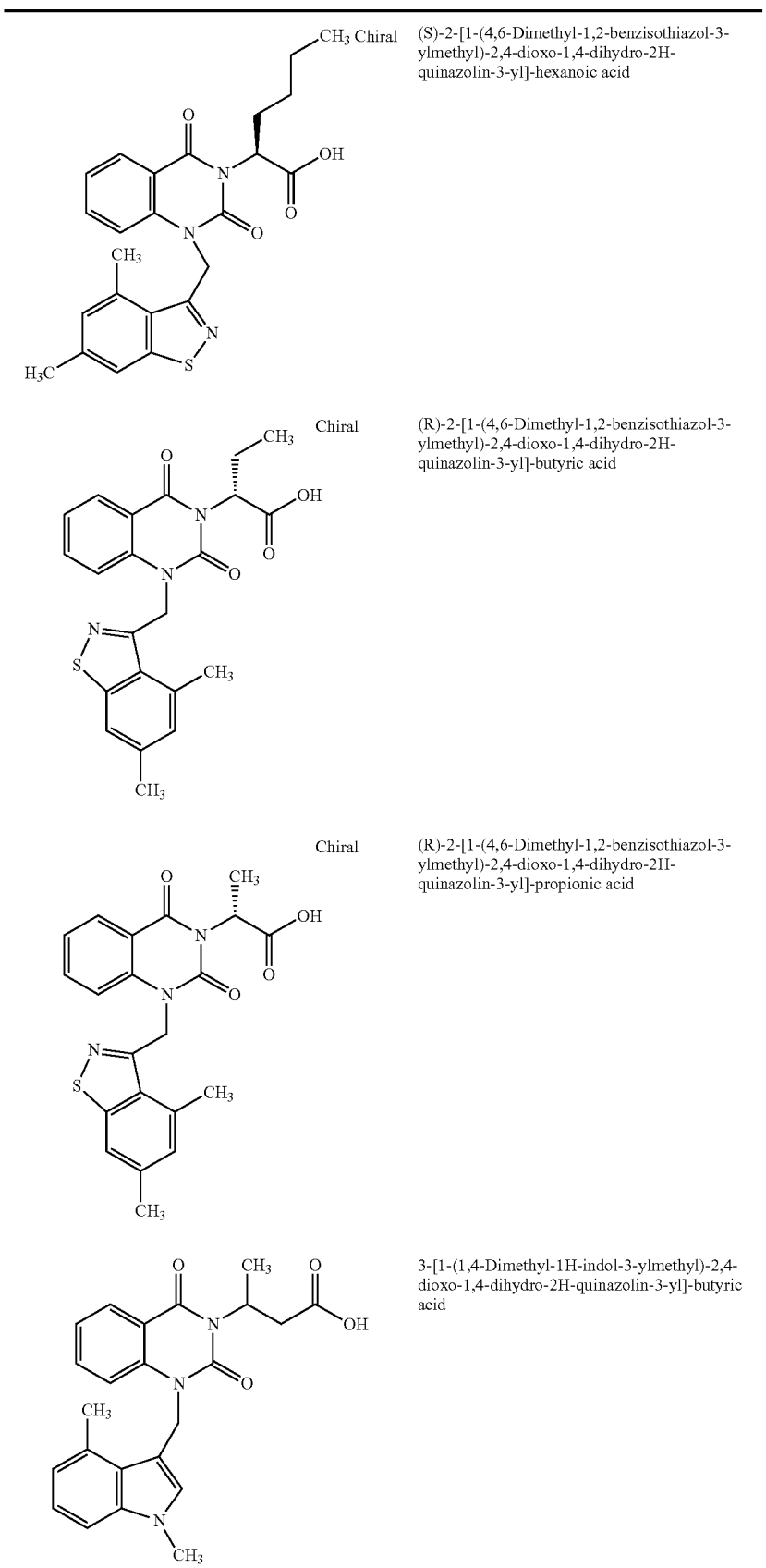

| Structure | | Name |
|---|---|---|
| | Chiral | (S)-2-[1-(4,6-Dimethyl-1,2-benzisothiazol-3-ylmethyl)-2,4-dioxo-1,4-dihydro-2H-quinazolin-3-yl]-hexanoic acid |
| | Chiral | (R)-2-[1-(4,6-Dimethyl-1,2-benzisothiazol-3-ylmethyl)-2,4-dioxo-1,4-dihydro-2H-quinazolin-3-yl]-butyric acid |
| | Chiral | (R)-2-[1-(4,6-Dimethyl-1,2-benzisothiazol-3-ylmethyl)-2,4-dioxo-1,4-dihydro-2H-quinazolin-3-yl]-propionic acid |
| | | 3-[1-(1,4-Dimethyl-1H-indol-3-ylmethyl)-2,4-dioxo-1,4-dihydro-2H-quinazolin-3-yl]-butyric acid |

TABLE 1-continued
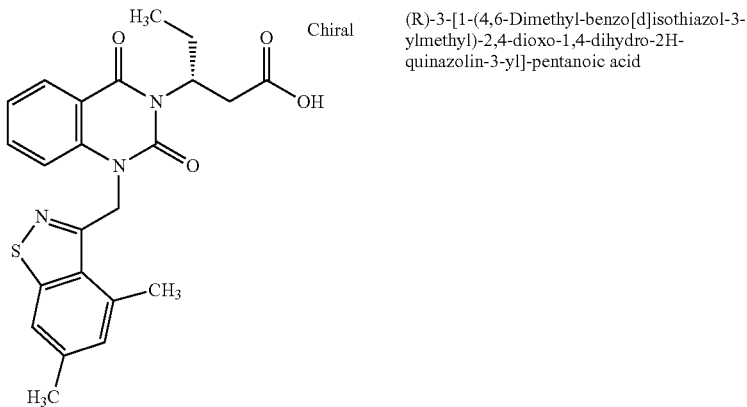
(R)-3-[1-(4,6-Dimethyl-benzo[d]isothiazol-3-ylmethyl)-2,4-dioxo-1,4-dihydro-2H-quinazolin-3-yl]-pentanoic acid
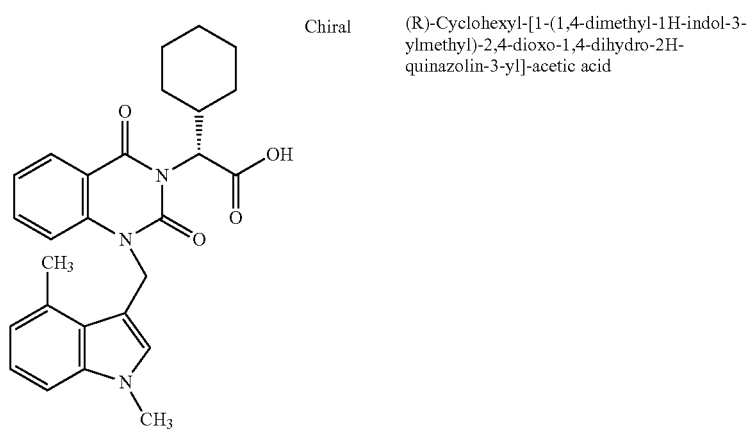
(R)-Cyclohexyl-[1-(1,4-dimethyl-1H-indol-3-ylmethyl)-2,4-dioxo-1,4-dihydro-2H-quinazolin-3-yl]-acetic acid
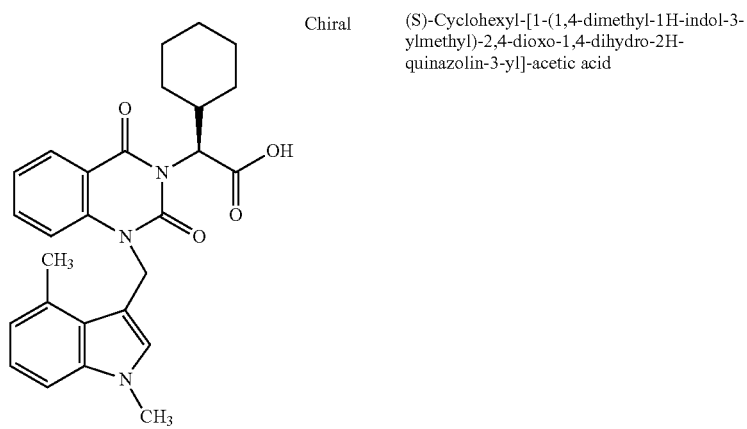
(S)-Cyclohexyl-[1-(1,4-dimethyl-1H-indol-3-ylmethyl)-2,4-dioxo-1,4-dihydro-2H-quinazolin-3-yl]-acetic acid TABLE 1-continued
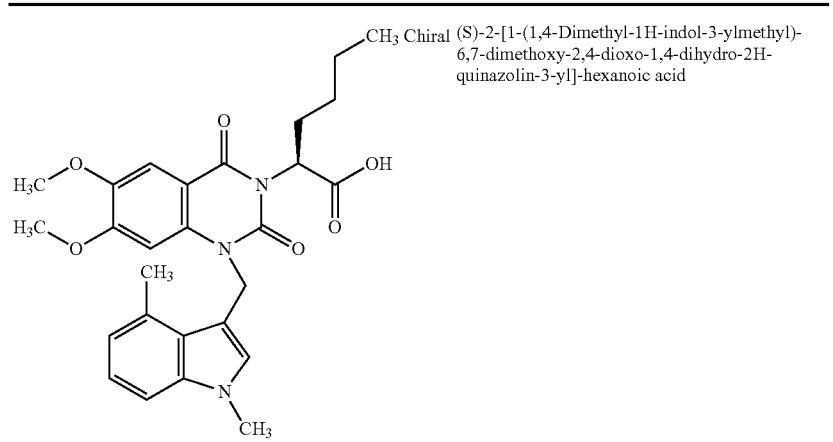
(S)-2-[1-(1,4-Dimethyl-1H-indol-3-ylmethyl)-6,7-dimethoxy-2,4-dioxo-1,4-dihydro-2H-quinazolin-3-yl]-hexanoic acid
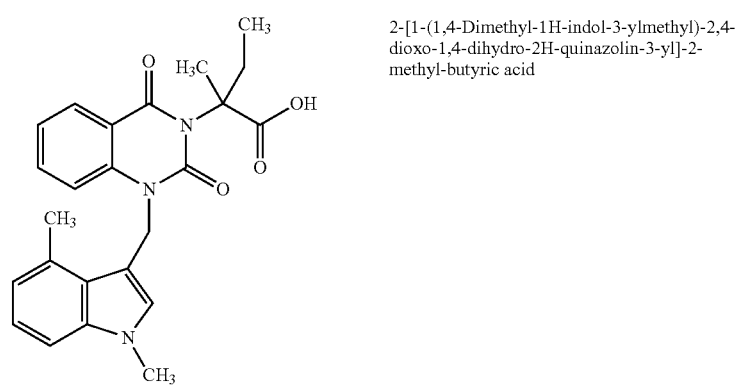
2-[1-(1,4-Dimethyl-1H-indol-3-ylmethyl)-2,4-dioxo-1,4-dihydro-2H-quinazolin-3-yl]-2-methyl-butyric acid
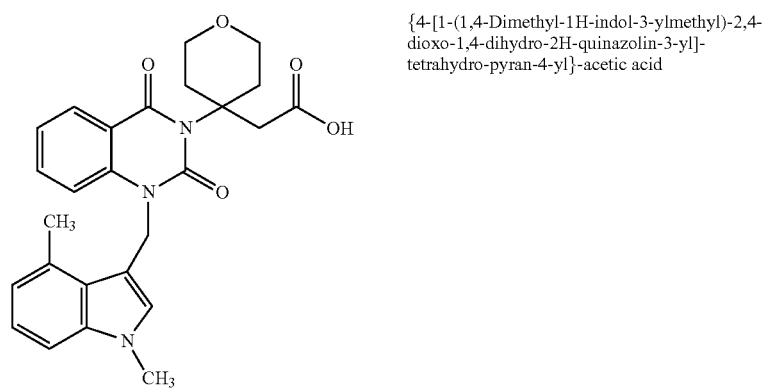
{4-[1-(1,4-Dimethyl-1H-indol-3-ylmethyl)-2,4-dioxo-1,4-dihydro-2H-quinazolin-3-yl]-tetrahydro-pyran-4-yl}-acetic acid
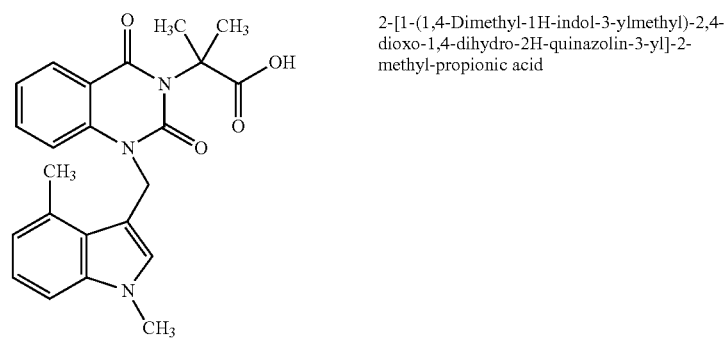
2-[1-(1,4-Dimethyl-1H-indol-3-ylmethyl)-2,4-dioxo-1,4-dihydro-2H-quinazolin-3-yl]-2-methyl-propionic acid TABLE 1-continued

| Structure | | Name |
|---|---|---|
| | Chiral | (R)-2-[1-(1,4-Dimethyl-1H-indol-3-ylmethyl)-2,4-dioxo-1,4-dihydro-2H-quinazolin-3-yl]-pentanoic acid amide |
| | | (R)-2-[1-(1,4-Dimethyl-1H-indol-3-ylmethyl)-2,4-dioxo-1,4-dihyd-2H-quinazolin-3-yl]-propionic acid methyl ester |
| | Chiral | (S)-2-[1-(1,4-Dimethyl-1H-indol-3-ylmethyl)-2,4-dioxo-1,4-dihydro-2H-quinazolin-3-yl]-propionic acid methyl ester |
| | Chiral | (R)-2-[1-(4,6-Dimethyl-1,2-benzisothiazol-3-ylmethyl)-2,4-dioxo-1,4-dihydro-2H-quinazolin-3-yl]-propionic acid methyl ester |

TABLE 1-continued

| | |
|---|---|
| 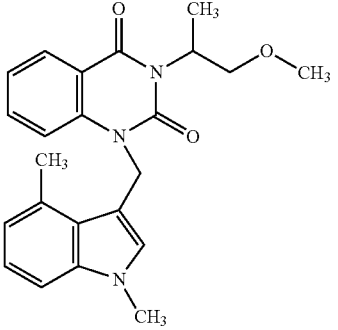 [SMILES: COCC(C)n1c(=O)c2ccccc2n(Cc2cn(C)c3cccc(C)c23)c1=O] | 1-(1,4-Dimethyl-1H-indol-3-ylmethyl)-3-(2-methoxy-l-methyl-ethyl)-1H-quinazoline-2,4-dione |
| Chiral 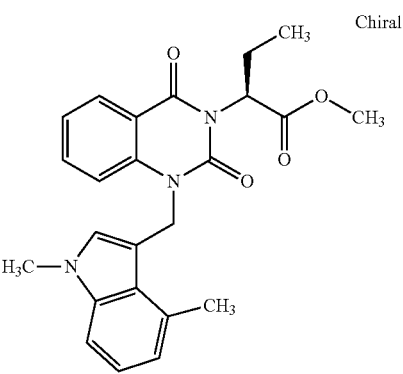 | (S)-2-[1-(1,4-Dimethyl-1H-indol-3-ylmethyl)-2,4-dioxo-1,4-dihydro-2H-quinazolin-3-yl]-butyric acid methyl ester |
| Chiral 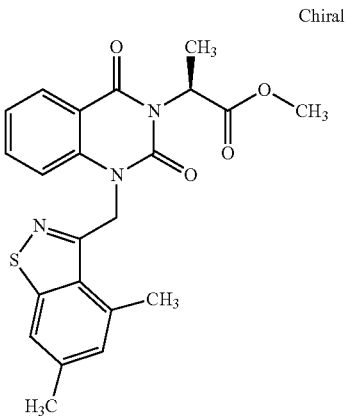 [SMILES: COC(=O)[C@H](C)n1c(=O)c2ccccc2n(Cc2nsc3cc(C)cc(C)c23)c1=O] | (S)-2-[1-(4,6-Dimethyl-1,2-benzisothiazol-3-ylmethyl)-2,4-dioxo-1,4-dihydro-2H-quinazolin-3-yl]propionic acid methyl ester |
| 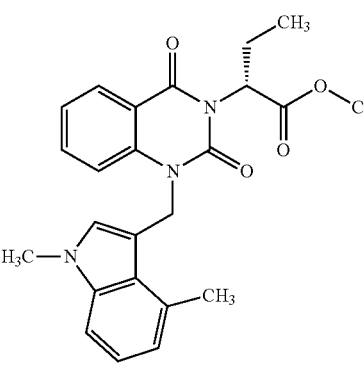 | (R)-2-[1-(1,4-Dimethyl-1H-indol-3-ylmethyl)-2,4-dioxo-1,4-dihydro-2H-quinazolin-3-yl]-butyric acid methyl ester |

TABLE 1-continued
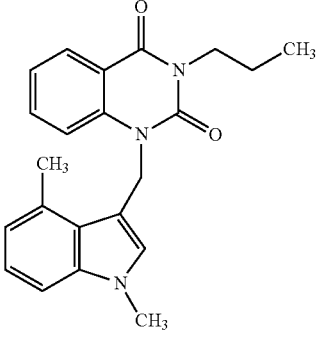 [SMILES: CCCn1c(=O)c2ccccc2n(Cc2cn(C)c3cccc(C)c23)c1=O]
1-(1,4-Dimethyl-1H-indol-3-ylmethyl)-3-propyl-1H-quinazoline-2,4-dione
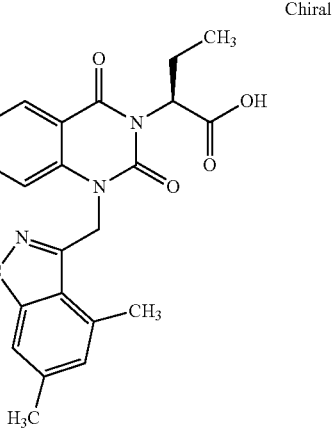
Chiral
(S)-2-[1-(4,6-Dimethyl-1,2-benzisothiazol-3-ylmethyl)-2,4-dioxo-1,4-dihydro-2H-quinazolin-3-yl]-butyric acid
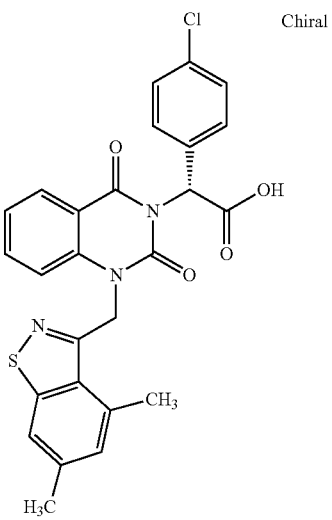 [SMILES: Cc1cc(C)c2c(Cn3c(=O)n([C@@H](C(=O)O)c4ccc(Cl)cc4)c(=O)c4ccccc43)nsc2c1]
Chiral
(R)-(4-Chloro-phenyl)-[1-(4,6-dimethyl-1,2-benzisothiazol-3-ylmethyl)-2,4-dioxo-1,4-dihydro-2H-quinazolin-3-yl]-acetic acid TABLE 1-continued

| Structure | Chirality | Name |
|---|---|---|
| 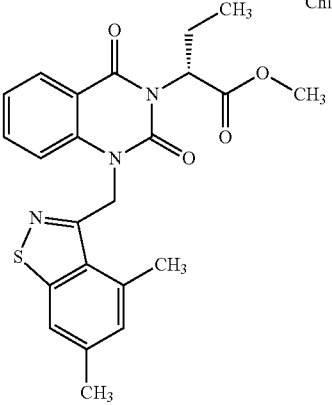 | Chiral | (R)-2-[1-(4,6-Dimethyl-1,2-benzisothiazol-3-ylmethyl)-2,4-dioxo-1,4-dihydro-2H-quinazolin-3-yl]-butyric acid methyl ester |
| 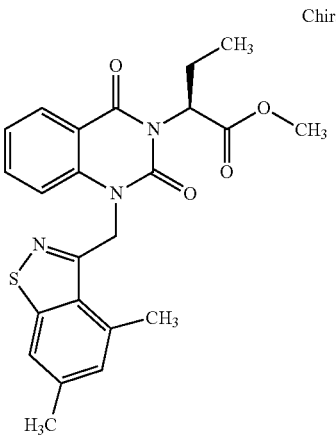 | Chiral | (S)-2-[1-(4,6-Dimethyl-1,2-benzisothiazol-3-ylmethyl)-2,4-dioxo-1,4-dihydro-2H-quinazolin-3-yl]-butyric acid methyl ester |
| 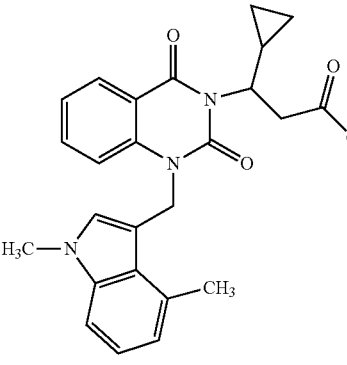 | | 3-Cyclopropyl-3-[1-(1,4-dimethyl-1H-indol-3-ylmethyl)-2,4-dioxo-1,4-dihydro-2H-quinazolin-3-yl]-propionic acid |
| 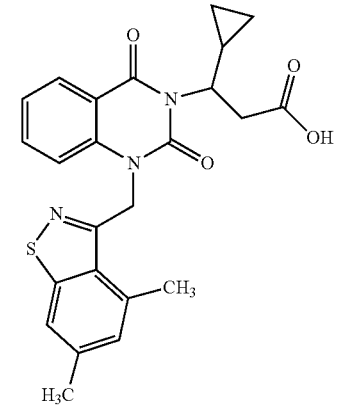 [SMILES: Cc1cc(C)c2c(Cn3c(=O)n(C(CC(=O)O)C4CC4)c(=O)c4ccccc43)nsc2c1] | | 3-Cyclopropyl-3-[1-(4,6-dimethyl-1,2-benzisothiazol-3-ylmethyl)-2,4-dioxo-1,4-dihydro-2H-quinazolin-3-yl]-propionic acid |

TABLE 1-continued

| Structure | Chirality | Name |
|---|---|---|
| 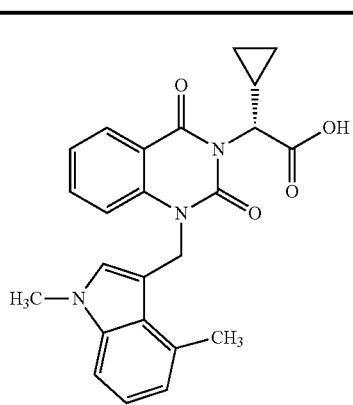 | Chiral | (R)-Cyclopropyl-[1-(1,4-dimethyl-1H-indol-3-ylmethyl)-2,4-dioxo-1,4-dihydro-2H-quinazolin-3-yl]-acetic acid |
| 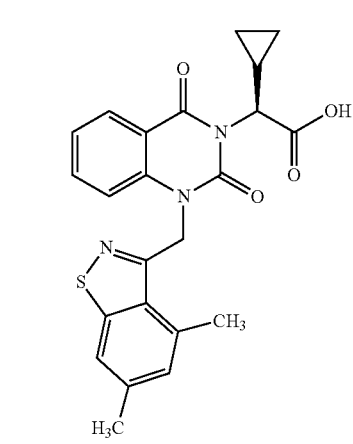 [SMILES: Cc1cc(C)c2c(Cn3c(=O)n([C@H](C(=O)O)C4CC4)c(=O)c4ccccc43)nsc2c1] | | (S)-Cyclopropyl-[1-(4,6-dimethyl-1,2-benzisothiazol-3-ylmethyl)-2,4-dioxo-1,4-dihydro-2H-quinazolin-3-yl]-acetic acid |
| 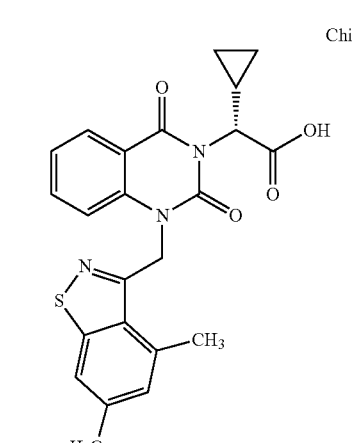 | Chiral | (R)-Cyclopropyl-[1-(4,6-dimethyl-1,2-benzisothiazol-3-ylmethyl)-2,4-dioxo-1,4-dihydro-2H-quinazolin-3-yl]-acetic acid |
| 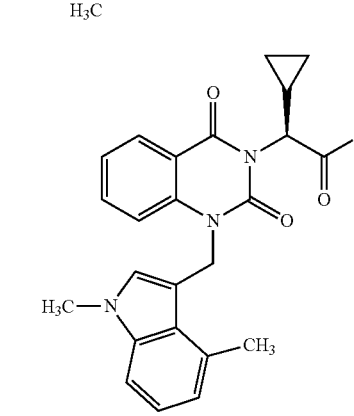 | | (S)-Cyclopropyl-[1-(1,4-dimethyl-1H-indol-3-ylmethyl)-2,4-dioxo-1,4-dihydro-2H-quinazolin-3-yl]acetic acid |

TABLE 1-continued

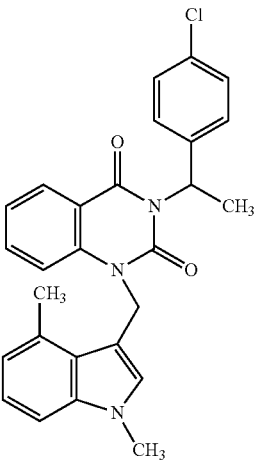 [SMILES: Cc1cccc2c1c(Cn1c(=O)n(C(C)c3ccc(Cl)cc3)c(=O)c3ccccc31)cn2C]

3-[1-(4-Chloro-phenyl)-ethyl]-1-(1,4-dimethyl-1H-indol-3-ylmethyl)-1H-quinazoline-2,4-dione
and

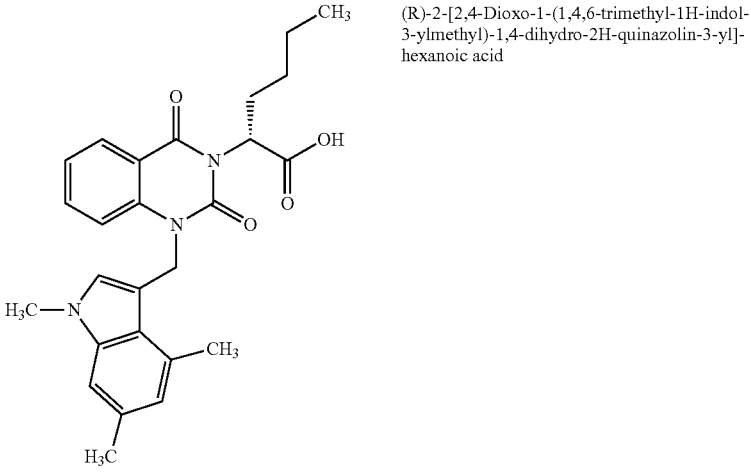

(R)-2-[2,4-Dioxo-1-(1,4,6-trimethyl-1H-indol-3-ylmethyl)-1,4-dihydro-2H-quinazolin-3-yl]-hexanoic acid or the pharmaceutically acceptable salts thereof.

The following is Chymase IC50 (nM) data for preferred formula (I) compounds of the invention:

TABLE II

|  | Chymase IC50 (nM) |
|---|---|
| (S)-2-[1-(1,4-Dimethyl-1H-indol-3-ylmethyl)-2,4-dioxo-1,4-dihydro-2H-quinazolin-3-yl]-pentanoic acid | 1.5 |
| (R)-2-[1-(1,4-Dimethyl-1H-indol-3-ylmethyl)-2,4-dioxo-1,4-dihydro-2H-quinazolin-3-yl]-hexanoic acid | 0.8 |
| (S)-2-[1-(1,4-Dimethyl-1H-indol-3-ylmethyl)-7-methoxy-2,4-dioxo-1,4-dihydro-2H-quinazolin-3-yl]-hexanoic acid | 4.9 |
| (R)-3-[1-(1,4-Dimethyl-1H-indol-3-ylmethyl)-2,4-dioxo-1,4-dihydro-2H-quinazolin-3-yl]-3-phenyl-propionic acid | 1 |
| (R)-[1-(1,4-Dimethyl-1H-indol-3-ylmethyl)-2,4-dioxo-1,4-dihydro-2H-quinazolin-3-yl]-phenyl-acetic acid | 1 |
| (S)-3-[1-(4,6-Dimethyl-benzo[d]isothiazol-3-ylmethyl)-2,4-dioxo-1,4-dihydro-2H-quinazolin-3-yl]-pentanoic acid | 3.7 |
| (R)-2-[1-(1,4-Dimethyl-1H-indol-3-ylmethyl)-2,4-dioxo-1,4-dihydro-2H-quinazolin-3-yl]-butyric acid | 1.4 |
| (R)-2-[2,4-Dioxo-1-(1,4,6-trimethyl-1H-indol-3-ylmethyl)-1,4-dihydro-2H-quinazolin-3-yl]-pentanoic acid | 0.27 |
| (R)-2-[1-(1,4-Dimethyl-1H-indol-3-ylmethyl)-6-methoxy-2,4-dioxo-1,4-dihydro-2H-quinazolin-3-yl]-hexanoic acid | 1.6 |
| 3-[1-(1,4-Dimethyl-1H-indol-3-ylmethyl)-2,4-dioxo-1,4-dihydro-2H-quinazolin-3-yl]-heptanoic acid | 4 |
| (R)-[1-(4,6-Dimethyl-1,2-benzisothiazol-3-ylmethyl)-2,4-dioxo-1,4-dihydro-2H-quinazolin-3-yl]-phenyl-acetic acid | 1.8 |

TABLE II-continued

| | Chymase IC50 (nM) |
|---|---|
| 2-[1-(1,4-Dimethyl-1H-indol-3-ylmethyl)-2,4-dioxo-1,4-dihydro-2H-quinazolin-3-yl]-pentanoic acid | 4 |
| {1-[1-(4,6-Dimethyl-1,2-benzisothiazol-3-ylmethyl)-2,4-dioxo-1,4-dihydro-2H-quinazolin-3-yl]-cyclohexyl}-acetic acid | 4 |
| 3-[1-(4,6-Dimethyl-1,2-benzisothiazol-3-ylmethyl)-2,4-dioxo-1,4-dihydro-2H-quinazolin-3-yl]-pentanoic acid | 2 |
| (S)-2-[1-(1,4-Dimethyl-1H-indol-3-ylmethyl)-2,4-dioxo-1,4-dihydro-2H-quinazolin-3-yl]-hexanoic acid | 2 |
| 2-[1-(1,4-Dimethyl-1H-indol-3-ylmethyl)-2,4-dioxo-1,4-dihydro-2H-quinazolin-3-yl]-hexanoic acid | 3 |
| {1-[1-(1,4-Dimethyl-1H-indol-3-ylmethyl)-2,4-dioxo-1,4-dihydro-2H-quinazolin-3-yl]-cyclohexyl}-acetic acid | 3 |
| {1-[1-(1,4-Dimethyl-1H-indol-3-ylmethyl)-2,4-dioxo-1,4-dihydro-2H-quinazolin-3-ylmethyl]-cyclohexyl}-acetic acid | 3 |
| (S)-2-[1-(1,4-Dimethyl-1H-indol-3-ylmethyl)-2,4-dioxo-1,4-dihydro-2H-quinazolin-3-yl]-propionic acid | 2.5 |
| (S)-2-[1-(1,4-Dimethyl-1H-indol-3-ylmethyl)-6-methoxy-2,4-dioxo-1,4-dihydro-2H-quinazolin-3-yl]-hexanoic acid | 2.6 |
| 4-[1-(1,4-Dimethyl-1H-indol-3-ylmethyl)-2,4-dioxo-1,4-dihydro-2H-quinazolin-3-yl]-3-phenyl-butyric acid | 3 |
| (R)-2-[1-(1,4-Dimethyl-1H-indol-3-ylmethyl)-2,4-dioxo-1,4-dihydro-2H-quinazolin-3-yl]-hexanoic acid | 3 |
| (R)-2-[1-(4,6-Dimethyl-1,2-benzisothiazol-3-ylmethyl)-2,4-dioxo-1,4-dihydro-2H-quinazolin-3-yl]-hexanoic acid | 3 |
| 1-[1-(1,4-Dimethyl-1H-indol-3-ylmethyl)-2,4-dioxo-1,4-dihydro-2H-quinazolin-3-ylmethyl]-cyclohexanecarboxylic acid | 3 |
| (S)-3-[1-(1,4-Dimethyl-1H-indol-3-ylmethyl)-2,4-dioxo-1,4-dihydro-2H-quinazolin-3-yl]-pentanoic acid | 3.2 |
| (S)-[1-(4,6-Dimethyl-1,2-benzisothiazol-3-ylmethyl)-2,4-dioxo-1,4-dihydro-2H-quinazolin-3-yl]-phenyl-acetic acid | 1 |
| (R)-3-[1-(1,4-Dimethyl-1H-indol-3-ylmethyl)-2,4-dioxo-1,4-dihydro-2H-quinazolin-3-yl]-pentanoic acid | 3.9 |
| 2-[1-(1,4-Dimethyl-1H-indol-3-ylmethyl)-2,4-dioxo-1,4-dihydro-2H-quinazolin-3-yl]-butyric acid | 4 |
| (S)-2-[1-(1,4-Dimethyl-1H-indol-3-ylmethyl)-2,4-dioxo-1,4-dihydro-2H-quinazolin-3-yl]-butyric acid | 1.7 |
| (S)-2-[1-(4,6-Dimethyl-1,2-benzisothiazol-3-ylmethyl)-6-methoxy-2,4-dioxo-1,4-dihydro-2H-quinazolin-3-yl]-hexanoic acid | 1.8 |
| (R)-2-[1-(1,4-Dimethyl-1H-indol-3-ylmethyl)-2,4-dioxo-1,4-dihydro-2H-quinazolin-3-yl]-propionic acid | 1.9 |
| (S)-[1-(1,4-Dimethyl-1H-indol-3-ylmethyl)-2,4-dioxo-1,4-dihydro-2H-quinazolin-3-yl]-phenyl-acetic acid | 2 |
| (S)-(4-Chloro-phenyl)-[1-(4,6-dimethyl-1,2-benzisothiazol-3-ylmethyl)-2,4-dioxo-1,4-dihydro-2H-quinazolin-3-yl]-acetic acid | 0.92 |

In all the compounds disclosed hereinabove in this application, in the event the nomenclature is in conflict with the structure, it shall be understood that the compound is defined by the structure.

The invention includes the use of any compounds of described above containing one or more asymmetric carbon atoms may occur as racemates and racemic mixtures, single enantiomers, diastereomeric mixtures, and individual diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes methods using all such tautomers.

All terms as used herein in this specification, unless otherwise stated, shall be understood in their ordinary meaning as known in the art. For example, $C_{1-4}$ alkoxy includes the organic radical $C_{1-4}$ alkyl with a terminal oxygen, such as methoxy, ethoxy, propoxy, butoxy.

All organic radicals: alkyl, alkenyl and alkynyl groups, or such groups which are incorporated in other radicals such as acyl and alkoxy, shall be understood as being branched or unbranched where structurally possible and unless otherwise specified, and may be partially or fully halogenated.

The term "lower" referred to above and hereinafter in connection with organic radicals or compounds respectively defines such as branched or unbranched with up to and including 7, preferably up to and including 4 and advantageously one or two carbon atoms.

A cyclic group shall be understood to mean carbocycle, heterocycle or heteroaryl, each may be partially or fully halogenated.

An acyl group is a radical defined as —C(O)—R, where R is an organic radical or a cyclic group. Acyl represents, for example, carbocyclic or heterocyclic aroyl, cycloalkylcarbonyl, (oxa or thia)-cycloalkylcarbonyl, lower alkanoyl, (lower alkoxy, hydroxy or acyloxy)-lower alkanoyl, (mono- or di-carbocyclic or heterocyclic)-(lower alkanoyl or lower alkoxy-, hydroxy- or acyloxy- substituted lower alkanoyl), or biaroyl.

Carbocycles include hydrocarbon rings containing from three to fourteen carbon atoms. These carbocycles may be either aromatic either aromatic or non-aromatic ring systems. The non-aromatic ring systems may be mono- or polyunsaturated, monocyclic, bicyclic or tricyclic and may be bridged. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, benzyl, indanyl, indenyl, benzocyclobutanyl, dihydronaphthyl, tetrahydronaphthyl, naphthyl, decahydronaphthyl, benzocycloheptanyl, adamantyl, norbornyl, fluorene, and benzocycloheptenyl. Certain terms for cycloalkyl such as cyclobutanyl and cyclobutyl shall be used interchangeably. Carbocycles shall be understood where structurally possible to be optionally partially or fully halogenated.

The term "heterocycle" refers to a stable nonaromatic 4-8 membered (but preferably, 5 or 6 membered) monocyclic or non-aromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Unless otherwise stated, heterocycles include but are not limited to, for example pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone.

The term "heteroaryl" shall be understood to mean an aromatic 5-6 membered monocyclic or 7-10 membered bicyclic ring containing 1-4 heteroatoms such as N, O and S. Unless otherwise stated, such heteroaryls include aziridinyl, thienyl, furanyl, isoxazolyl, oxazolyl, thiazolyl, thiadiazolyl, pyrazolyl, pyrrolyl, imidazolyl, pyridinyl, pyrimidinyl, pyrazinyl, pyridazinyl, pyranyl, indolyl, azaindolyl, isoindolyl, benzoxazolyl, benzothiazolyl, benzisothiazolyl, benzimidazolyl, isoquinolinyl, quinolinyl, benzofuranyl, benzodioxolyl, indazolyl or triazolyl.

The term "heteroatom" as used herein shall be understood to mean atoms other than carbon such as oxygen, nitrogen, sulfur and phosphorous.

As used herein, "nitrogen" and "sulfur" include any oxidized form of nitrogen and sulfur and the quaternized form of any basic nitrogen. All heteroatoms in open chain or cyclic radicals include all oxidized forms.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative and/or is partially or fully halogenated. For example, quinolinyl may include decahydroquinolinyl and tetrahydroquinolinyl, naphthyl may include its hydrogenated derivatives such as tetrahydranaphthyl. Other partially or fully hydrogenated derivatives of the aryl and heteroaryl compounds described herein will be apparent to one of ordinary skill in the art.

The term "halogen" as used in the present specification shall be understood to mean bromine, chlorine, fluorine or iodine, preferably fluorine. The definitions "partially or fully halogenated"; partially or fully fluorinated; "substituted by one or more halogen atoms", includes for example, mono, di or tri halo derivatives on one or more carbon atoms. For alkyl, a nonlimiting example would be —$CH_2CHF_2$, —$CF_3$ etc.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—$(C_1-C_4$ alkyl$)_4^+$ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds described herein are either commercially available or can be made by methods and any necessary intermediates well known in the art.

In order that this invention may be more fully understood, the following examples are set forth. These examples are for the purpose of illustrating preferred embodiments of this invention, and are not to be construed as limiting the scope of the invention in any way.

The examples which follow are illustrative and, as recognized by one skilled in the art, particular reagents or conditions could be modified as needed for individual compounds without undue experimentation. Starting materials used in the scheme below are either commercially available or easily prepared from commercially available materials by those skilled in the art.

General Synthetic Methods

The invention also provides processes for making compounds of Formula (I). In the scheme, unless specified otherwise, R1, R2, R3, R4, R5, Ar, m and n in the formulas below shall have the meaning of R1, R2, R3, R4, R5, Ar, m and n in Formula (I) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization.

The appropriately substituted starting materials and intermediates used in the preparation of compounds of the invention are either commercially available or readily prepared by methods known in the literature to those skilled in the art, and are illustrated in the synthetic examples below.

Compounds of Formula (1) may be synthesized by the method illustrated in Scheme 1.

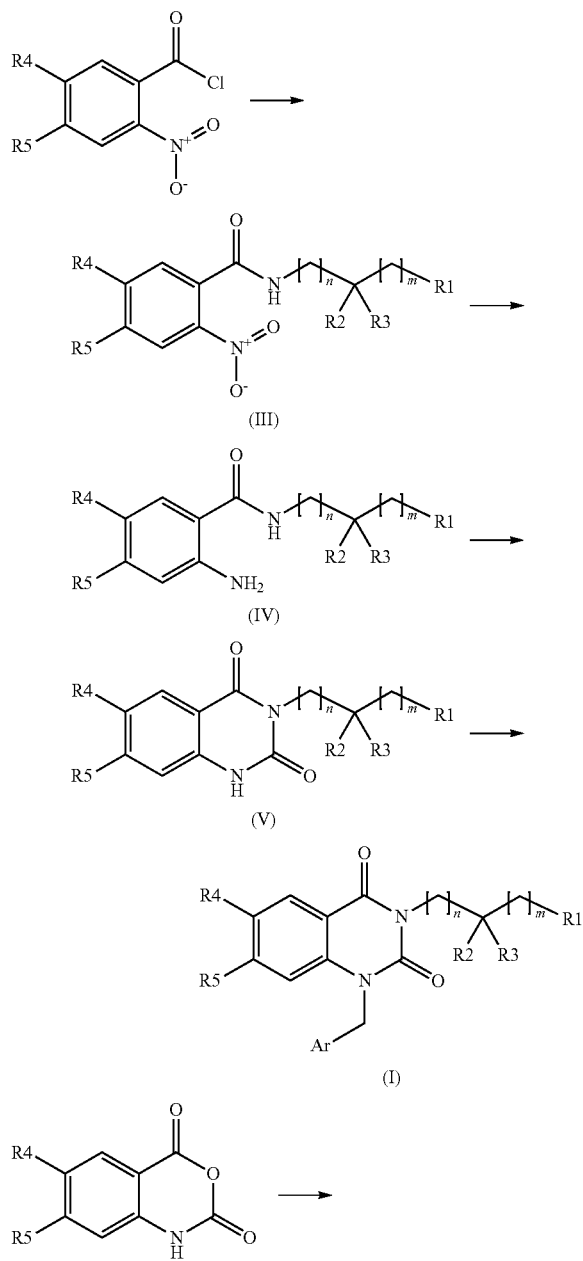

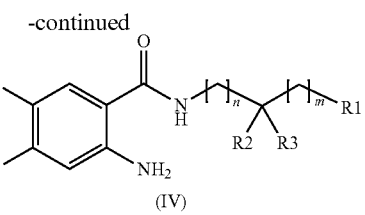

Reaction of an optionally substituted 2-nitrobenzoyl chloride with an amine, in a suitable solvent, provides a 2-nitrobenzamide compound of formula (III). Reduction of the nitro group to an amino group, using standard procedures, provides the corresponding 2-aminobenzamide compound of formula (IV). Cyclization of the compound of formula (IV) using suitable reagents, such as phosgene, diphosgene, CDI or trichloromethyl chloroformate, provides a quinazolinedione compound of formula (V). Reaction of the compound of formula (V) with Ar—$CH_2$—X, wherein X=halogen or quaternary ammonium salt, provides a compound of formula (I).

Alternatively, the intermediate compound of formula (IV) is synthesized by reaction of an optionally substituted isotonic anhydride with an amine in a suitable solvent.

Further modification of the initial product of formula (I) by methods known in the art and illustrated in the Examples below, may be used to prepare additional compounds of this invention.

EXAMPLES

Example 1

(R)-Cyclohexyl-[1-(1,4-dimethyl-1H-indol-3-ylmethyl)-2,4-dioxo-1,4-dihydro-2H-quinazolin-3-yl]-acetic acid To a mixture of 2-nitrobenzoyl chloride (0.5 mL, 3.69 mmol) and (R)-amino-cyclohexyl-acetic acid methyl ester hydrochloride (1.0 g, 4.82 mmol), (prepared according to example A), in dichloromethane (10 mL) is added diisopropyl ethylamine (DIPEA) (1.5 mL, 8.61 mmol). The mixture is stirred at room temperature for 16 hours. The reaction mixture is concentrated and the resulting residue is purified by flash chromatography with 40% EtOAc in Hexane as the eluent to afford (R)-cyclohexyl-(2-nitro-benzoylamino)-acetic acid methyl ester (1.16 g, 98%).

A mixture of (R)-cyclohexyl-(2-nitro-benzoylamino)-acetic acid methyl ester (1.16 g, 3.62 mmol), 10% Pd/C (250 mg) in EtOH (25 mL) are stirred under $H_2$ atmosphere at room temperature for 16 hours. The reaction mixture is filtered and the organic layer is concentrated to give (R)-(2-amino-benzoylamino)-cyclohexyl-acetic acid methyl ester (1.08 g, 98%).

To a solution of (R)-(2-amino-benzoylamino)-cyclohexyl-acetic acid methyl ester (1.08 g, 3.72 mmol) in THF (30 mL) is added trichloromethyl chloroformate (550 mg, 2.78 mmol). The mixture is stirred at 90° C. for 4 hours. The reaction mixture is allowed to cool to room temperature, diluted with EtOAc (100 mL) and washed with $H_2O$ (50 mL×3). The organic layer is dried over sodium sulfate and is concentrated to give the desired (R)-cyclohexyl-(2,4-dioxo-1,4-dihydro-2H-quinazolin-3-yl)-acetic acid methyl ester (1.17 g, 99%).

To a mixture of (R)-cyclohexyl-(2,4-dioxo-1,4-dihydro-2H-quinazolin-3-yl)-acetic acid methyl ester (100 mg, 0.32 mmol) and (1,4-dimethyl-1H-indol-3-ylmethyl)-trimethylammonium iodide (160 mg, 0.47 mmol) in DMF (2.5 mL) is added potassium carbonate ($K_2CO_3$) (100 mg, 0.72 mmol). The mixture is stirred at 60° C. for 4 hours. The reaction mixture is allowed to cool to room temperature, dilute with EtOAc (50 mL) and is washed with $H_2O$ (50 mL×3). The organic layer is dried over sodium sulfate and concentrated. The resulting residue is triturated with EtOAc and hexanes to afford (R)-cyclohexyl-[1-(1,4-dimethyl-1H-indol-3-ylmethyl)-2,4-dioxo-1,4-dihydro-2H-quinazolin-3-yl]-acetic acid methyl ester (124 mg, 94%).

To a solution of (R)-cyclohexyl-[1-(1,4-dimethyl-1H-indol-3-ylmethyl)-2,4-dioxo-1,4-dihydro-2H-quinazolin-3-yl]-acetic acid methyl ester (124 mg, 0.26 mmol) in dioxane (2.5 ml) is added a solution of LiOH monohydrate (25 mg, 0.60 mmol) in $H_2O$ (2.5 mL). The solution is stirred at 60° C. for 16 hours. The reaction mixture is allowed to cool to room temperature, quenched with 4M HCl in dioxane (500 µL) and is concentrated. The resulting residue is purified by flash chromatography with 3.5% MeOH in dichloromethane as the eluent to afford the title compound. LCMS (ESMS): m/z 460.86 (M+H$^+$)

The following compounds are synthesized using a similar procedure.

(S)-2-[1-(1,4-Dimethyl-1H-indol-3-ylmethyl)-2,4-dioxo-1,4-dihydro-2H-quinazolin-3-yl]-butyric acid; LCMS (ESMS): m/z 406 (M+H$^+$)

(R)-2-[1-(1,4-Dimethyl-1H-indol-3-ylmethyl)-2,4-dioxo-1,4-dihydro-2H-quinazolin-3-yl]-butyric acid; LCMS (ESMS): m/z 406 (M+H$^+$)

{-[1-(1,4-Dimethyl-1H-indol-3-ylmethyl)-2,4-dioxo-1,4-dihydro-2H-quinazolin-3-yl]-cyclohexyl}-acetic acid. LCMS (ESMS): m/z 446.19 (M+H$^+$)

2-[1-(1,4-Dimethyl-1H-indol-3-ylmethyl)-2,4-dioxo-1,4-dihydro-2H-quinazolin-3-yl]-2-methyl-butyric acid. LCMS (ESMS): m/z 419.99 (M+H$^+$)

3-[1-(1,4-Dimethyl-1H-indol-3-ylmethyl)-2,4-dioxo-1,4-dihydro-2H-quinazolin-3-yl]-butyric acid. LCMS (ESMS): m/z 406.07 (M+H$^+$)

(R)-[1-(1,4-Dimethyl-1H-indol-3-ylmethyl)-2,4-dioxo-1,4-dihydro-2H-quinazolin-3-yl]-phenyl-acetic acid. LCMS (ESMS): m/z 454.16 (M+H$^+$)

{4-[1-(1,4-Dimethyl-1H-indol-3-ylmethyl)-2,4-dioxo-1,4-dihydro-2H-quinazolin-3-yl]-tetrahydro-pyran-4-yl}-acetic acid. LCMS (ESMS): m/z 462.13 (M+H$^+$).

(S)-Cyclohexyl-[1-(1,4-dimethyl-1H-indol-3-ylmethyl)-2,4-dioxo-1,4-dihydro-2H-quinazolin-3-yl]-acetic acid. LCMS (ESMS): m/z 460.87 (M+H$^+$).

(R)-Cyclohexyl-[1-(1,4-dimethyl-1H-indol-3-ylmethyl)-2,4-dioxo-1,4-dihydro-2H-quinazolin-3-yl]-acetic acid. LCMS (ESMS): m/z 460.86 (M+H$^+$).

The following compounds are synthesized according to example 1, step 1 to 4:

(S)-2-[1-(1,4-Dimethyl-1H-indol-3-ylmethyl)-2,4-dioxo-1,4-dihydro-2H-quinazolin-3-yl]-butyric acid methyl ester; LCMS (ESMS): m/z 420 (M+H$^+$)

(R)-2-[1-(1,4-Dimethyl-1H-indol-3-ylmethyl)-2,4-dioxo-1,4-dihydro-2H-quinazolin-3-yl]-butyric acid methyl ester; LCMS (ESMS): m/z 420 (M+H$^+$)

Example 2

2-[1-(1,4-Dimethyl-1H-indol-3-ylmethyl)-2,4-dioxo-1,4-dihydro-2H-quinazolin-3-yl]-pentanoic acid To a mixture of isatoic anhydride (750 mg, 4.60 mmol) and 2-amino-pentanoic acid methyl ester hydrochloride (1.4 g, 8.35 mmol) (prepared according to example C), in DMF (10 mL) is added triethylamine (2.0 mL, 14.30 mmol). The mixture is stirred at room temperature for 16 hours. The reaction mixture is diluted with EtOAc (100 mL) and is washed with $H_2O$ (50 mL×3). The organic layer is dried over sodium sulfate, concentrated and the resulting residue is purified by flash chromatography with 35% EtOAc in Hexane as the eluent to afford the desired 2-(2-amino-benzoylamino)-pentanoic acid methyl ester (575 mg, 50%).

To a solution of 2-(2-amino-benzoylamino)-pentanoic acid methyl ester (575 mg, 2.30 mmol) and 1,1'-carbonyldiimidazole (930 mg, 5.74 mmol) in THF (25 mL) is added 1,8-diazabicyclo[5.4.0]undec-7-ene (0.9 mL, 6.02 mmol). The mixture is stirred at room temperature for 16 hours. The reaction mixture is diluted with EtOAc (100 mL) and is washed with $H_2O$ (50 mL×3). The organic layer is dried over sodium sulfate, concentrated and the resulting residue is purified by flash chromatography with 50% EtOAc in Hexane as the eluent to afford the desired 2-(2,4-dioxo-1,4-dihydro-2H-quinazolin-3-yl)-pentanoic acid methyl ester (284 mg, 45%).

To a mixture of 2-(2,4-dioxo-1,4-dihydro-2H-quinazolin-3-yl)-pentanoic acid methyl ester (120 mg, 0.43 mmol) and (1,4-dimethyl-1H-indol-3-ylmethyl)-trimethylanmonium iodide (190 mg, 0.55 mmol) in DMF (2.5 mL) is added $K_2CO_3$ (180 mg, 1.30 mmol). The mixture is stirred at 60° C. for 4 hours. The reaction mixture is allowed to cool to room temperature, diluted with EtOAc (50 mL) and is washed with $H_2O$ (50 mL×3). The organic layer is dried over sodium sulfate and is concentrated. The resulting residue is triturated with EtOAc and hexanes to afford the desired 2-[1-(1,4-dimethyl-1H-indol-3-ylmethyl)-2,4-dioxo-1,4-dihydro-2H-quinazolin-3-yl]-pentanoic acid methyl ester (108 mg, 57%).

To a solution of 2-[1-(1,4-dimethyl-1H-indol-3-ylmethyl)-2,4-dioxo-1,4-dihydro-2H-quinazolin-3-yl]-pentanoic acid methyl ester (108 mg, 0.25 mmol) in dioxane (2.5 ml) is added a solution of LiOH monohydrate (25 mg, 0.60 mmol) in $H_2O$ (2.5 mL). The solution is stirred at 60° C. for 16 hours. The reaction mixture is allowed to cool to room temperature, quenched with 4M HCl in dioxane (400 µl) and is concentrated. The resulting residue is triturated with MeOH and $H_2O$ to afford the title compound. LCMS (ESMS): m/z 420.21 (M+H$^+$).

The following compounds are synthesized using a similar procedure.

3-Cyclopropyl-3-[1-(1,4-dimethyl-1H-indol-3-ylmethyl)-2,4-dioxo-1,4-dihydro-2H-quinazolin-3-yl]-propionic acid; LCMS (ESMS): m/z 432 (M+H$^+$)

(R)-Cyclopropyl-[1-(1,4-dimethyl-1H-indol-3-ylmethyl)-2,4-dioxo-1,4-dihydro-2H-quinazolin-3-yl]-acetic acid. LCMS (ESMS): m/z 418 (M+H$^+$)

(S)-Cyclopropyl-[1-(1,4-dimethyl-1H-indol-3-ylmethyl)-2,4-dioxo-1,4-dihydro-2H-quinazolin-3-yl]-acetic acid; LCMS (ESMS): m/z 418 (M+H$^+$)

3-[1-(1,4-Dimethyl-1H-indol-3-ylmethyl)-2,4-dioxo-1,4-dihydro-2H-quinazolin-3-yl]-pentanoic acid. LCMS (ESMS): m/z 420.21 (M+H$^+$)

2-[1-(1,4-Dimethyl-1H-indol-3-ylmethyl)-2,4-dioxo-1,4-dihydro-2H-quinazolin-3-yl]-hexanoic acid. LCMS (ESMS): m/z 434.23 (M+H$^+$)

2-[1-(1,4-Dimethyl-1H-indol-3-ylmethyl)-2,4-dioxo-1,4-dihydro-2H-quinazolin-3-yl]-butyric acid. LCMS (ESMS): m/z 406.20 (M+H$^+$)

3-[1-(1,4-Dimethyl-1H-indol-3-ylmethyl)-2,4-dioxo-1,4-dihydro-2H-quinazolin-3-yl]-heptanoic acid. LCMS (ESMS): m/z 448.24 (M+H$^+$)

1-[1-(1,4-Dimethyl-1H-indol-3-ylmethyl)-2,4-dioxo-1,4-dihydro-2H-quinazolin-3-ylmethyl]-cyclohexanecarboxylic acid. LCMS (ESMS): m/z 460.18 (M+H$^+$).

Example 3

{1-[1-(1,4-Dimethyl-1H-indol-3-ylmethyl)-2,4-di-oxo-1,4-dihydro-2H-quinazolin-3-ylmethyl]-cyclo-hexyl}-acetic acid To a mixture of 2-nitrobenzoyl chloride (0.3 mL, 2.05 mmol) and (1-aminomethyl-cyclohexyl)-acetic acid methyl ester hydrochloride (500 mg, 2.25 mmol) (prepares according to example A) in dichloromethane (10 mL) is added DIPEA (0.75 mL, 4.02 mmol). The mixture is stirred at room temperature for 16 hours. The reaction mixture is concentrated and the resulting residue is purified by flash chromatography with 50% EtOAc in Hexane as the eluent to afford the desired {1-[(2-nitro-benzoylamino)-methyl]-cyclohexyl}-acetic acid methyl ester (680 mg, 99%).

A mixture of {1-[(2-nitro-benzoylamino)-methyl]-cyclohexyl}-acetic acid methyl ester (680 mg, 2.03 mmol), 10% Pd/C (120 mg) in EtOH (25 mL) is stirred under $H_2$ atmosphere at room temperature for 16 hours. The reaction mixture is filtered and the organic layer is concentrated to give the desired {1-[(2-amino-benzoylamino)-methyl]-cyclohexyl}-acetic acid methyl ester (619 mg, 100%).

To a solution of {1-[(2-amino-benzoylamino)-methyl]-cyclohexyl}-acetic acid methyl ester (620 mg, 2.04 mmol) and 1,1'-carbonyldiimidazole (660 mg, 4.07 mmol) in THF (25 mL) is added 1,8-diazabicyclo[5.4.0]undec-7-ene (0.6 mL, 4.01 mmol). The mixture is stirred at room temperature for 16 hours. The reaction mixture is diluted with EtOAc (100 mL) and is washed with $H_2O$ (50 mL×3). The organic layer is dried over sodium sulfate, and is concentrated to afford the desired [1-(2,4-dioxo-1,4-dihydro-2H-quinazolin-3-ylmethyl)-cyclohexyl]-acetic acid methyl ester (670 mg, 99%).

To a mixture of [1-(2,4-dioxo-1,4-dihydro-2H-quinazol-ylmethyl)-cyclohexyl]-acetic acid methyl ester (107 mg, 0.32 mmol) and (1,4-dimethyl-1H-indol-3-ylmethyl)-trimethylammonium iodide (170 mg, 0.49 mmol) in DMF (2.5 mL) is added $K_2CO_3$ (100 mg, 0.72 mmol). The mixture is stirred at 60° C. for 4 hours. The reaction mixture is allowed to cool to room temperature, dilute with EtOAc (50 mL) and is washed with $H_2O$ (50 mL×3). The organic layer is dried over sodium sulfate and is concentrated. The resulting residue is triturated with EtOAc and hexanes to afford the desired {1-[1-(1,4-dimethyl-1H-indol-3-ylmethyl)-2,4-dioxo-1,4-dihydro-2H-quinazolin-3-ylmethyl]-cyclohexyl}-acetic acid methyl ester (63 mg, 40%).

To a solution of {1-[1-(1,4-dimethyl-1H-indol-3-ylmethyl)-2,4-dioxo-1,4-dihydro-2H-quinazolin-3-ylmethyl]-cyclohexyl}-acetic acid methyl ester (63 mg, 0.13 mmol) in dioxane (2.5 ml) is added a solution of LiOH monohydrate (25 mg, 0.60 mmol) in $H_2O$ (2.5 mL). The solution is stirred at 60° C. for 16 hours. The reaction mixture is allowed to cool to room temperature, quenches with 4M HCl in dioxane (500 μL) and is concentrated. The resulting residue is purified by flash chromatography with 6% MeOH in dichloromethane as the eluent to afford the title compound. LCMS (ESMS): m/z 474.18 (M+H$^+$)

The following compounds are synthesized using a similar procedure.

4-[1-(1,4-Dimethyl-1H-indol-3-ylmethyl)-2,4-dioxo-1,4-dihydro-2H-quinazolin-3-yl]-3-phenyl-butyric acid. LCMS (ESMS): m/z 482.15 (M+H$^+$).

(R)-3-[1-(1,4-Dimethyl-1H-indol-3-ylmethyl)-2,4-dioxo-1,4-dihydro-2H-quinazolin-3-yl]-pentanoic acid. LCMS (ESMS): m/z 420.2 (M+H$^+$)

(S)-3-[1-(1,4-Dimethyl-1H-indol-3-ylmethyl)-2,4-dioxo-1,4-dihydro-2H-quinazolin-3-yl]-pentanoic acid. LCMS (ESMS): m/z 420.1 (M+H$^+$)

Example 4

(S)-[1-(1,4-Dimethyl-1H-indol-3-ylmethyl)-2,4-di-oxo-1,4-dihydro-2H-quinazolin-3-yl]-phenyl-acetic acid To a mixture of isatoic anhydride (250 mg, 1.53 mmol) and (S)-2-phenylglycine methyl ester hydrochloride (370 mg, 1.84 mmol) in DMF (5.0 mL) is added triethylamine (0.29 mL, 2.07 mmol). The mixture is stirred at room temperature for 16 hours. The reaction mixture is diluted with EtOAc (100 mL) and is washed with $H_2O$ (50 mL×3). The organic layer is dried over sodium sulfate and concentrated to afford (S)-(2-amino-benzoylamino)-phenyl-acetic acid methyl ester (330 mg, 76%).

To a solution of (S)-(2-amino-benzoylamino)-phenyl-acetic acid methyl ester (330 mg, 1.16 mmol) in THF (30 mL) is added trichloromethyl chloroformate (115 mg, 0.58 mmol). The mixture is stirred at 90° C. for 16 hours. The reaction mixture is allowed to cool to room temperature, diluted with EtOAc (100 mL) and is washed with $H_2O$ (50 mL×3). The organic layer is dried over sodium sulfate and concentrated to give the (S)-(2,4-dioxo-1,4-dihydro-2H-quinazolin-3-yl)-phenyl-acetic acid methyl ester (110 mg, 31%).

To a mixture of (S)-(2,4-dioxo-1,4-dihydro-2H-quinazolin-3-yl)-phenyl-acetic acid methyl ester (110 mg, 0.35 mmol) and (1,4-dimethyl-1H-indol-3-ylmethyl)-trimethylammonium iodide (180 mg, 0.52 mmol) in DMF (2.5 mL) is added $K_2CO_3$ (150 mg, 1.09 mmol). The mixture is stirred at 60° C. for 4 hours. The reaction mixture is allowed to cool to room temperature, dilutes with EtOAc (50 mL) and is washed with $H_2O$ (50 mL×3). The organic layer is dried over sodium sulfate and is concentrated. The resulting residue is purified by flash chromatography with 50% EtOAc in hexanes as the eluent to afford (S)-[1-(1,4-dimethyl-1H-indol-3-ylmethyl)-2,4-dioxo-1,4-dihydro-2H-quinazolin-3-yl]-phenyl-acetic acid methyl ester (100 mg, 60%).

To a solution of (S)-[1-(1,4-dimethyl-1H-indol-3-ylmethyl)-2,4-dioxo-1,4-dihydro-2H-quinazolin-3-yl]-phenyl-acetic acid methyl ester (100 mg, 0.21 mmol) in dioxane (2.5 ml) is added a solution of LiOH monohydrate (25 mg, 0.60 mmol) in $H_2O$ (2.5 mL). The solution is stirred at 60° C. for 4 hours. The reaction mixture is allowed to cool to room temperature, quenched with 4M HCl in dioxane (500 μL) and is concentrated. The resulting residue is purified by flash chromatography with 10% MeOH in dichloromethane as the eluent to afford the title compound. LCMS (ESMS): m/z 454.19 (M+H$^+$).

The following compounds are synthesized using a similar procedure.

(R)-2-[1-(1,4-Dimethyl-1H-indol-3-ylmethyl)-2,4-dioxo-1,4-dihydro-2H-quinazolin-3-yl]-propionic acid; LCMS (ESMS): m/z 392 (M+H$^+$).

(S)-3-[1-(1,4-Dimethyl-1H-indol-3-ylmethyl)-2,4-dioxo-1,4-dihydro-2H-quinazolin-3-yl]-propionic acid; LCMS (ESMS): m/z 392 (M+H$^+$).

(S)-3-[1-(1,4-Dimethyl-1H-indol-3-ylmethyl)-2,4-dioxo-1,4-dihydro-2H-quinazolin-3-yl]-hexanoic acid. LCMS (ESMS): m/z 434.12 (M+H$^+$).

2-[1-(1,4-Dimethyl-1H-indol-3-ylmethyl)-2,4-dioxo-1,4-dihydro-2H-quinazolin-3-yl]-2-methyl-propionic acid. LCMS (ESMS): m/z 406.23 (M+H$^+$).

(R)-3-[1-(1,4-Dimethyl-1H-indol-3-ylmethyl)-2,4-dioxo-1,4-dihydro-2H-quinazolin-3-yl]-3-phenyl-propionic acid. LCMS (ESMS): m/z 468.27 (M+H$^+$).

(S)-3-[1-(1,4-Dimethyl-1H-indol-3-ylmethyl)-2,4-dioxo-1,4-dihydro-2H-quinazolin-3-yl]-3-phenyl-propionic acid. LCMS (ESMS): m/z 468.22 (M+H$^+$).

1-[1-(1,4-Dimethyl-1H-indol-3-ylmethyl)-2,4-dioxo-1,4-dihydro-2H-quinazolin-3-yl]-cyclohexanecarboxylic acid. LCMS (ESMS): m/z 446.19 (M+H$^+$)

(S)-2-[1-(1,4-Dimethyl-1H-indol-3-ylmethyl)-2,4-dioxo-1,4-dihydro-2H-quinazolin-3-yl]-hexanoic acid. LCMS (ESMS): m/z 434.15 (M+H$^+$).

(R)-2-[1-(1,4-Dimethyl-1H-indol-3-ylmethyl)-2,4-dioxo-1,4-dihydro-2H-quinazolin-3-yl]-hexanoic acid. LCMS (ESMS): m/z 434.15 (M+H$^+$).

(S)-2-[1-(1,4-Dimethyl-1H-indol-3-ylmethyl)-2,4-dioxo-1,4-dihydro-2H-quinazolin-3-yl]-pentanoic acid. LCMS (ESMS): m/z 420.13 (M+H$^+$).

(R)-2-[1-(1,4-Dimethyl-1H-indol-3-ylmethyl)-2,4-dioxo-1,4-dihydro-2H-quinazolin-3-yl]-pentanoic acid. LCMS (ESMS): m/z 420.11 (M+H$^+$).

The following compounds are synthesized according to example 4, step 1 to 4:

(R)-2-[1-(1,4-Dimethyl-1H-indol-3-ylmethyl)-2,4-dioxo-1,4-dihydro-2H-quinazolin-3-yl]-propionic acid methyl ester; LCMS (ESMS): m/z 406 (M+H$^+$)

(S)-2-[1-(1,4-Dimethyl-1H-indol-3-ylmethyl)-2,4-dioxo-1,4-dihydro-2H-quinazolin-3-yl]-propionic acid methyl ester; LCMS (ESMS): m/z 406 (M+H$^+$)

Example 5

3-[1-(4,6-Dimethyl-1,2-benzisothiazol-3-ylmethyl)-2,4-dioxo-1,4-dihydro-2H-quinazolin-3-yl]-pentanoic acid To a solution of AlCl$_3$ (0.4 g, 3.6 mmol) in CH$_2$Cl$_2$ (4 mL) at −20° C. under nitrogen are added 3,5-dimethylbenzenethiol (1 g, 7.2 mmol) and oxalyl chloride (0.6 mL, 7.2 mmol) respectively. The solution is warmed to room temperature for 1 hour and is heated to 120° C. in a microwave reactor for 15 minutes. The solution is cooled and is poured into crushed ice. The solution is extracted with CH$_2$Cl$_2$ and the organic layer is collected. The solution is dried with MgSO$_4$ and is filtered. The filtrate is concentrated and the residue is purified by flash chromatography with 5% EtOAc in Hexane as the eluent to afford 4,6-dimethyl-benzo[b]thiophene-2,3-dione (500 mg, 35%).

To a solution of 4,6-dimethyl-benzo[b]thiophene-2,3-dione (100 mg, 0.5 mmol) in NH$_3$ in MeOH (5 mL) is added 30% H$_2$O$_2$ (0.17 mL, 1.6 mmol) dropwise at room temperature. The solution is stirred at the same temperature for 2 hours. The solution is concentrated and the residue is purified by flash chromatography with 20% EtOAc in Hexane as the eluent to afford 4,6-dimethyl-1,2-benzisothiazole-3-carboxylic acid amide (35 mg, 33%) as a pale red solid.

To a solution of 4,6-dimethyl-1,2-benzisothiazole-3-carboxylic acid amide (20 mg, 0.097 mmol) in EtOH (10 mL) and H$_2$O (2 mL) is added KOH (11'mg, 0.19 mmol). The solution is heated to 85° C. for 48 hours. The solution is cooled down and is placed in an ice bath. Conc. HCl is added to adjust the pH of the solution to 2. The precipitated solid is collected by means of filtration to afford 4,6-Dimethyl-1,2-benzisothiazole-3-carboxylic acid (15 mg, 75%).

To a solution of 4,6-dimethyl-1,2-benzisothiazole-3-carboxylic acid (10 mg, 0.048 mmol) in MeOH (5 mL) is added conc. H$_2$SO$_4$ (0.1 mL) at room temperature. The solution is heated at 60° C. for 24 hours. The solution is cooled and neutralized with saturated NaHCO$_3$. The solution is extracted with EtOAc. The combined organic layer is dried with MgSO$_4$ and is filtered. The filtrate is concentrated and the residue is purified by flash chromatography with 20% EtOAc in Hexane as the eluent to afford the desirable product: 4,6-Dimethyl-1,2-benzisothiazole-3-carboxylic acid methyl ester (10 mg, 94%) as colorless oil.

To a solution of 4,6-dimethyl-1,2-benzisothiazole-3-carboxylic acid methyl ester (600 mg, 2.7 mmol) in THF (20 mL) is added LiBH$_4$ (118 mg, 5.4 mmol) at 0° C. under a nitrogen atmosphere. The solution is stirred at the same temperature for 1 hour. Saturated NaHCO$_3$ is added and the solution is extracted with EtOAc. The combined organic layer is dried with MgSO$_4$ and is filtered. The filtrate is concentrated and the residue is used in the next step of the synthesis without further purification.

To a solution of (4,6-dimethyl-1,2-benzisothiazol-3-yl)-methanol (100 mg, 0.5 mmol) in CH$_2$Cl$_2$ (15 mL) are added PPh$_3$ (200 mg, 0.78 mmol) and CBr$_4$ (340 mg, 1 mmol) at room temperature. The solution is stirred at the same temperature for 1 hour. The solution is concentrated and the residue is purified by flash chromatography with 10% EtOAc in Hexane as the eluent to afford 3-bromomethyl-4,6-dimethyl-1,2-benzisothiazole (90 mg, 68%) as a white solid.

To a solution of 3-(2,4-dioxo-1,4-dihydro-2H-quinazolin-3-yl)-pentanoic acid methyl ester (50 mg, 0.18 mmol) (prepared according to example 2, steps 1-2) in DMF (10 mL) are added 3-bromomethyl-4,6-dimethyl-1,2-benzisothiazole (70 mg, 0.271 mmol) and K$_2$CO$_3$ (50 mg, 0.36 mmol) at room temperature under a nitrogen atmosphere. The solution is heated at 100° C. for 2 hours. The solution is cooled down and water is added. The solution is extracted with EtOAc and the combined organic layer is dried with MgSO$_4$. The solution is filtered and the filtrate is concentrated. The residue is purified by flash chromatography with 20% EtOAc in Hexane as the eluent to afford 3-[1-(4,6-Dimethyl-1,2-benzisothiazol-3-ylmethyl)-2,4-dioxo-1,4-dihydro-2H-quinazolin-3-yl]-pentanoic acid methyl ester (65 mg, 80%) as a colorless foam.

To a solution of 3-[1-(4,6-dimethyl-1,2-benzisothiazol-3-ylmethyl)-2,4-dioxo-1,4-dihydro-2H-quinazolin-3-yl]-pentanoic acid methyl ester (65 mg, 0.14 mmol) in 1,4-dioxane (10 mL), THF (5 mL) and water (2 mL) is added LiOH (7 mg, 0.29 mmol) at room temperature. The solution is stirred at room temperature for 8 hours. The solution is concentrated and water is added to the residue. The solution is acidified by 12N HCl in an ice-bath. The precipitated solid filtration to afford the title compound.: LCMS (ESMS): m/z 438.09 (M+H$^+$).

The following compounds are synthesized using a similar procedure:

(R)-Cyclopropyl-[1-(4,6-dimethyl-1,2-benzisothiazol-3-ylmethyl)-2,4-dioxo-1,4-dihydro-2H-quinazolin-3-yl]-acetic acid. LCMS (ESMS): m/z 436 (M+H$^+$)

(S)-Cyclopropyl-[1-(4,6-dimethyl-1,2-benzisothiazol-3-ylmethyl)-2,4-dioxo-1,4-dihydro-2H-quinazolin-3-yl]-acetic acid; LCMS (ESMS): m/z 436 (M+H$^+$).

3-Cyclopropyl-3-[1-(4,6-dimethyl-1,2-benzisothiazol-3-ylmethyl)-2,4-dioxo-1,4-dihydro-2H-quinazolin-3-yl]-propionic acid; LCMS (ESMS): m/z 450 (M+H$^+$).

(S)-[1-(4,6-Dimethyl-1,2-benzisothiazol-3-ylmethyl)-2,4-dioxo-1,4-dihydro-2H-quinazolin-3-yl]-phenyl-acetic acid. LCMS (ESMS): m/z 472.75 (M+H$^+$).

Example 6

(S)-(4-Chloro-phenyl)-[1-(4,6-dimethyl-1,2-benzisothiazol-3-ylmethyl)-2,4-dioxo-1,4-dihydro-2H-quinazolin-3-yl]-acetic acid To a solution of (S)-(4-Chloro-phenyl)-(2,4-dioxo-1,4-dihydro-2H-quinazolin-3-yl)-acetic acid ethyl ester (50 mg, 0.14 mmol) (prepared according to example 1, steps 1-3) in DMF (10 mL) are added 3-Bromomethyl-4,6-dimethyl-1,2-benzisothiazole (54 mg, 0.21 mmol) (prepares according to example 5, steps 1-6) and $K_2CO_3$ (58 mg, 0.42 mmol) at room temperature under nitrogen atmosphere. The solution is heated to 100° C. for 2 hours. The solution is cooled down and water is added. The solution is extracted with EtOAc and the combined organic layer is dried with $MgSO_4$. The solution is filtered and the filtrate is concentrated. The residue is purified by flash chromatography with 20% EtOAc in Hexane as the eluent to afford (S)-(4-Chloro-phenyl)-[1-(4,6-dimethyl-1,2-benzisothiazol-3-ylmethyl)-2,4-dioxo-1,4-dihydro-2H-quinazolin-3-yl]-acetic acid ethyl ester (50 mg, 67%) as a colorless foam.

To a solution of (S)-(4-Chloro-phenyl)-[1-(4,6-dimethyl-1,2-benzisothiazol-3-ylmethyl)-2,4-dioxo-1,4-dihydro-2H-quinazolin-3-yl]-acetic acid ethyl ester (50 mg, 0.094 mmol) in 1,4-dioxane (10 mL) and water (1 mL) is added LiOH (6.7 mg, 0.28 mmol) at room temperature. The solution is stirred at the same temperature for 4 hours. The solution is concentrated and water is added to the residue. The solution is acidified by 12N HCl in an ice-bath. The precipitated solid is collected by filtration to afford the title compound.: LCMS (ESMS): m/z 506.10 (M+H$^+$)

The following compounds are synthesized using a similar procedure:
- (R)-(4-Chloro-phenyl)-[1-(4,6-dimethyl-1,2-benzisothiazol-3-ylmethyl)-2,4-dioxo-1,4-dihydro-2H-quinazolin-3-yl]-acetic acid. LCMS (ESMS): m/z 506.15 (M+H$^+$)
- {1-[1-(4,6-Dimethyl-1,2-benzisothiazol-3-ylmethyl)-2,4-dioxo-1,4-dihydro-2H-quinazolin-3-yl]-cyclohexyl}acetic acid. LCMS (ESMS): m/z 478.16 (M+H$^+$)
- (R)-3-[1-(4,6-Dimethyl-benzo[d]isothiazol-3-ylmethyl)-2,4-dioxo-1,4-dihydro-2H-quinazolin-3-yl]-pentanoic acid. LCMS (ESMS): m/z 438.2 (M+H$^+$)
- (S)-3-[1-(4,6-Dimethyl-benzo[d]isothiazol-3-ylmethyl)-2,4-dioxo-1,4-dihydro-2H-quinazolin-3-yl]-pentanoic acid. LCMS (ESMS): m/z 438.2 (M+H$^+$)
- (S)-2-[1-(4,6-Dimethyl-1,2-benzisothiazol-3-ylmethyl)-2,4-dioxo-1,4-dihydro-2H-quinazolin-3-yl]-butyric acid. LCMS (ESMS): m/z 424.0 (M+H$^+$)
- (R)-2-[1-(4,6-Dimethyl-1,2-benzisothiazol-3-ylmethyl)-2,4-dioxo-1,4-dihydro-2H-quinazolin-3-yl]-butyric acid; LCMS (ESMS): m/z 424 (M+H$^+$).
- (R)-[1-(4,6-Dimethyl-1,2-benzisothiazol-3-ylmethyl)-2,4-dioxo-1,4-dihydro-2H-quinazolin-3-yl]-phenyl-acetic acid. LCMS (ESMS): m/z 472.75 (M+H$^+$).

The following compounds are synthesized according to example 6, step 1:
- (R)-2-[1-(4,6-Dimethyl-1,2-benzisothiazol-3-ylmethyl)-2,4-dioxo-1,4-dihydro-2H-quinazolin-3-yl]-butyric acid methyl ester; LCMS (ESMS): m/z 438 (M+H$^+$)
- (S)-2-[1-(4,6-Dimethyl-1,2-benzisothiazol-3-ylmethyl)-2,4-dioxo-1,4-dihyiro-2H-quinazolin-3-yl]-butyric acid methyl ester; LCMS (ESMS): m/z 438 (M+H$^+$)

Example 7

(R)-3-[1-(4,6-Dimethyl-1,2-benzisothiazol-3-ylmethyl)-2,4-dioxo-1,4-dihydro-2H-quinazolin-3-yl]-butyric acid (R)-3-(2,4-Dioxo-1,4-dihydro-2H-quinazolin-3-yl)-butyric acid methyl ester (124 mg, 0.5 mmol) (prepared according to example 4, steps 1-2), 3-bromomethyl-4,6-dimethyl-1,2-benzisothiazole (150 mg, 0.59 mmol) (prepared according to example 5, steps 1-6), and potassium carbonate (345.5 mg, 2.5 mmol) are combined in a reaction vial and DMF (1 mL) is added. The reaction mixture is agitated at ambient temperature for 18 hours then diluted with water (15 mL). The product is isolated by filtration and purified by flash chromatography using an ethyl acetate/hexane gradient to provide (R)-3-[1-(4,6-dimethyl-1,2-benzisothiazol-3-ylmethyl)-2,4-dioxo-1,4-dihydro-2H-quinazolin-3-yl]-butyric acid methyl ester (196 mg, 93%).

To a solution of (R)-3-[1-(4,6-dimethyl-1,2-benzisothiazol-3-ylmethyl)-2,4-dioxo-1,4-dihydro-2H-quinazolin-3-yl]-butyric acid methyl ester (60 mg, 0.14 mmol) in THF (1 mL) is added a solution of LiOH (8.5 mg, 0.20 mmol) in water (0.5 mL) and the resulting mixture is agitated at ambient temperature for 24 hours, heated at 50° C. for 6 hours, then agitated an additional 48 hours at ambient temperature. The reaction mixture is neutralized with 1N HCl (0.2 mL) then extracted with ethyl acetate (2×10 mL). The combined extracts are washed with water (1×10 mL) and brine (1×10 mL), dried with sodium sulfate and concentrated to provide the title compound. LCMS (ESMS): m/z 410 (M+H$^+$).

The following compounds are synthesized using a similar procedure.
- (S)-2-[1-(4,6-Dimethyl-1,2-benzisothiazol-3-ylmethyl)-2,4-dioxo-1,4-dihydro-2H-quinazolin-3-yl]-propionic acid; LCMS (ESMS): m/z 410 (M+H$^+$)
- (S)-2-[1-(4,6-Dimethyl-1,2-benzisothiazol-3-ylmethyl)-2,4-dioxo-1,4-dihydro-2H-quinazolin-3-yl]-hexanoic acid. LCMS (ESMS): m/z 452.74 (M+H$^+$)
- (R)-2-[1-(4,6-Dimethyl-1,2-benzisothiazol-3-ylmethyl)-2,4-dioxo-1,4-dihydro-2H-quinazolin-3-yl]-hexanoic acid. LCMS (ESMS): m/z 452.74 (M+H$^+$).

The following compounds are synthesized according to example 7, step 1
- (S)-2-[ 1 -(4,6-Dimethyl-1,2-benzisothiazol-3-ylmethyl)-2,4-dioxo-1,4-dihydro-2H-quinazolin-3-yl]-propionic acid methyl ester; LCMS (ESMS): m/z 424 (M+H$^+$).\
- (R)-2-[1-(4,6-Dimethyl-1,2-benzisothiazol-3-ylmethyl)-2,4-dioxo-1,4-dihydro-2H-quinazolin-3-yl]-propionic acid methyl ester; LCMS (ESMS): m/z 424 (M+H$^+$)

Example 8

(R)-2-[2,4-Dioxo-1-(1,4,6-trimethyl-1H-indol-3-ylmethyl)-1,4-dihydro-2H-quinazolin-3-yl]-pentanoic acid A solution of the 4,6-dimethylindole (750 mg, 5.2 mmol) in DMF (20 mL) is cooled to 0° C. under nitrogen and is treated with 60% sodium hydride in mineral oil (413 mg, 10.3 mmol). After stirring for 15 minutes the iodomethane (0.4 mL, 6.2 mmol) is introduced and the cooling bath is removed. After 30 minutes the solution is quenched with water (5 ml) and then concentrates to reduce the volume of DMF. The reaction is poured into a mixture of water (200 mL) and EtOAc (100 mL). The layers are separated and the aqueous phase is extracted with EtOAc (3×200 mL). The combined organics are washed with water (3×), dried (MgSO$_4$), filtered and concentrated. The residue is purified by flash chromatography with 10% EtOAc in Hexane as the eluent to afford 1,4,6-Trimethyl-1H-indole (700 mg, 80%) as a white solid.

A solution of 1,4,6-trimethyl-1H-indole (800 mg, 5 mmol) in DMF (0.9 mL) is cooled to 5° C. under nitrogen. Pyrophosphoryl chloride (1.4 mL, 10 mmol) is then slowly introduced. Upon complete addition the cooling bath is removed and the reaction is allowed to warm to ambient temperature. After a total of 45 minutes, the reaction is recooled to 5° C. and is slowly quenched with 2N NaOH. The pH of the solution is adjusted to 8. The precipitated solid is collected by filtration and is washed with water to afford 1,4,6-Trimethyl-1H-indole-3-carbaldehyde (875 mg, 93%).

To a solution of 1,4,6-trimethyl-1H-indole-3-carbaldehyde (875 mg, 4.7 mmol) in CH$_2$Cl$_2$ (30 mL) and dimethylamine (2.0 M solution in MeOH) (4.7 mL, 9.3 mmol) is added NaBH(OAc)$_3$ (2.9 g, 14 mmol) at 0° C. Upon complete addition the cooling bath is removed and the reaction mixture is stirred at room temperature for 48 hours. When the reaction is complete, the mixture is diluted with CH$_2$Cl$_2$ and is washed with saturated NaHCO$_3$. The layers are separated and the organic phase is dried over MgSO$_4$, filters and is concentrated. The residue is used in the next step of the synthesis without purification.

To a stirred solution of dimethyl-(1,4,6-trimethyl-1H-indol-3-ylmethyl)-amine (910 mg, 4.2 mmol) in acetonitrile (10 mL) is added iodomethane (0.3 mL, 5 mmol) at room temperature. The solution is stirred at the same temperature for 5 hours. The solution is concentrated and the resulting white solid is washed with small amount of cold Et$_2$O and is collected by filtration. The resulting white solid; Trimethyl-(1,4,6-trimethyl-1H-indol-3-ylmethyl)-amino iodide (1 g, 66%) is used in the next step of the synthesis without further purification.

To a solution of (R)-2-(2,4-Dioxo-1,4-dihydro-2H-quinazolin-3-yl)-pentanoic acid methyl ester (50 mg, 0.18 mmol) (prepared according to example 1, steps 1-3) in DMF (10 mL) are added trimethyl-(1,4,6-trimethyl-1H-indol-3-ylmethyl)-amino iodide (97 mg, 0.27 mmol) and K$_2$CO$_3$ (50 mg, 0.36 mmol) at room temperature. The solution is heated to 100° C. for 4 hours. The solution is cooled and is extracted with water and EtOAc. The combined organic layer is dried with MgSO$_4$ and is filtered. The filtrate is concentrated and the residue is purified by flash chromatography with 20% EtOAc in Hexane as the eluent to afford (R)-2-[2,4-dioxo-1-(1,4,6-trimethyl-1H-indol-3-ylmethyl)-1,4-dihydro-2H-quinazolin-3-yl]-pentanoic acid methyl ester (65 mg, 80%) as a white foam.

To a solution of (R)-2-[2,4-dioxo-1-(1,4,6-trimethyl-1H-indol-3-ylmethyl)-1,4-dihydro-2H-quinazolin-3-yl]-pentanoic acid methyl ester (50 mg, 0.11 mmol) in 1,4-dioxane (10 mL) and water (2 mL) is added LiOH (5.4 mg, 0.22 mmol) at room temperature. The solution is stirred at 60° C. for 4 hours. The solution is concentrated and water is added to the residue. The solution is acidified by 12N HCl in an ice-bath. The precipitated white solid is collected by filtration and is dried under vacuum to afford the title product. : LCMS (ESMS): m/z 434.89 (M+H$^+$).

The following compound is synthesized using a similar procedure:
(R)-2-[2,4-Dioxo-1-(1,4,6-trimethyl-1H-indol-3-ylmethyl)-1,4-dihydro-2H-quinazolin-3-yl]-hexanoic acid. LCMS (ESMS): m/z 448.91 (M+H$^+$)

Example 9

3-[1-(1,4-Dimethyl-1H-indol-3-ylmethyl)-2,4-dioxo-1,4-dihydro-2H-quinazolin-3-yl]-4-phenyl-butyric acid To a solution of 2-amino-4-methoxy-benzoic acid (1.0 g, 5.98 mmol) and 1,1'-carbonyldiimidazole (980 mg, 6.04 mmol) in pyridine (5 mL) is added 1,8-diazabicyclo[5.4.0]undec-7-ene (0.9 mL, 6.02 mmol). The mixture is stirred at room temperature for 2 hours follows by the addition of (S)-2-amino-hexanoic acid methyl ester hydrochloride (1.1 g, 6.06 mmol). The reaction mixture is stirred at room temperature for 16 hours and diluted with EtOAc (100 mL), the solution is washed with H$_2$O (50 mL×3). The organic layer is dried over sodium sulfate, and is concentrated. The resulting residue is purified by flash chromatography with 60% EtOAc in hexanes as the eluent to afford (S)-2-(2-amino-4-methoxy-benzoylamino)-hexanoic acid methyl ester (1.03 g, 59%).

To a solution of (S)-2-(2-amino-4-methoxy-benzoylamino)-hexanoic acid methyl ester (1.0 g, 3.50 mmol) in THF (30 mL) is added trichloromethyl chloroformate (325 mg, 1.64 mmol). The mixture is stirred at 90° C. for 4 hours. The reaction mixture is allowed to cool to room temperature, diluted with EtOAc (100 mL) and washed with H$_2$O (50 mL×3). The organic layer is dried over sodium sulfate and concentrated to give (S)-2-(7-methoxy-2,4-dioxo-1,4-dihydro-2H-quinazolin-3-yl)-hexanoic acid methyl ester (1.1 g, 98%).

To a mixture of (S)-2-(7-methoxy-2,4-dioxo-1,4-dihydro-2H-quinazolin-3-yl)-hexanoic acid methyl ester (100 mg, 0.31 mmol) and (1,4-dimethyl-1H-indol-3-ylmethyl)-trimethylammonium iodide (160 mg, 0.47 mmol) in DMF (2.5 mL) is added K$_2$CO$_3$ (100 mg, 0.72 mmol). The mixture is stirred at 60° C. for 4 hours. The reaction mixture is allowed to cool to room temperature, diluted with EtOAc (50 mL) and washed with H$_2$O (50 mL×3). The organic layer is dried over sodium sulfate and concentrated. The resulting residue is triturated with EtOAc and hexanes to afford (S)-2-[1-(1,4-dimethyl-1H-indol-3-ylmethyl)-7-methoxy-2,4-dioxo-1,4-dihydro-2H-quinazolin-3-yl]-hexanoic acid methyl ester (145 mg, 97%).

To a solution of (S)-2-[1-(1,4-dimethyl-1H-indol-3-ylmethyl)-7-methoxy-2,4-dioxo-1,4-dihydro-2H-quinazolin-3-yl]-hexanoic acid methyl ester (145 mg, 0.30 mmol) in dioxane (2.5 ml) is added a solution of LiOH monohydrate (50 mg, 1.19 mmol) in H$_2$O (2.5 mL). The resulting mixture is stirred at 60° C. for 4 hours. The reaction mixture is allowed to cool to room temperature, quenched with 4M HCl in dioxane (500 µL) and is concentrated. The resulting residue is triturated with H$_2$O and MeOH to afford (S)-2-[1-(1,4-dimethyl-1H-indol-3-ylmethyl)-7-methoxy-2,4-dioxo-1,4-dihydro-2H-quinazolin-3-yl]-hexanoic acid. LCMS (ESMS): m/z 464.22 (M+H$^+$).

Example 10

(S)-2-[1-(1,4-Dimethyl-1H-indol-3-ylmethyl)-6-methoxy-2,4-dioxo-1,4-dihydro-2H-quinazolin-3-yl]-hexanoic acid To a mixture of 5-methoxy-isatoic anhydride (1.0 g, 5.18 mmol) and (S)-2-amino-hexanoic acid methyl ester hydrochloride (1.4 g, 7.71 mmol) (prepared according to example A) in DMF (10 mL) is added triethylamine (2.0 mL, 11.48 mmol). The mixture is stirred at room temperature for 16 hours. The reaction mixture is diluted with EtOAc (100 mL)

and washed with H$_2$O (50 mL×3). The organic layer is dried over sodium sulfate, concentrated and the residue is purified by flash chromatography with 60% EtOAc in Hexane as the eluent to afford (S)-2-(2-amino-5-methoxy-benzoylamino)-hexanoic acid methyl ester (410 mg, 27%).

To a solution of (S)-2-(2-amino-5-methoxy-benzoylamino)-hexanoic acid methyl ester (410 mg, 1.39 mmol) in THF (30 mL) is added trichloromethyl chloroformate (200 mg, 1.01 mmol). The mixture is stirred at 90° C. for 4 hours. The reaction mixture is allowed to cool to room temperature, diluted with EtOAc (100 mL) and washed with H$_2$O (50 mL×3). The organic layer is dried over sodium sulfate and is concentrated to give (S)-2-(6-methoxy-2,4-dioxo-1,4-dihydro-2H-quinazolin-3-yl)-hexanoic acid methyl ester (440 mg, 98%).

To a mixture of (S)-2-(6-methoxy-2,4-dioxo-1,4-dihydro-2H-quinazolin-3-yl)-hexanoic acid methyl ester (100 mg, 0.31 mmol) and (1,4-dimethyl-1H-indol-3-ylmethyl)-trimethylammonium iodide (160 mg, 0.47 mmol) in DMF (2.5 mL) is added K$_2$CO$_3$ (100 mg, 0.72 mmol). The mixture is stirred at 60° C. for 4 hours. The reaction mixture is allowed to cool to room temperature, diluted with EtOAc (50 mL) and washed with H$_2$O (50 mL×3). The organic layer is dried over sodium sulfate and is concentrated. The resulting residue is triturated with EtOAc and hexanes to afford (S)-2-[1-(1,4-dimethyl-1H-indol-3-ylmethyl)-6-methoxy-2,4-dioxo-1,4-dihydro-2H-quinazolin-3-yl]-hexanoic acid methyl ester (143 mg, 96%).

To a solution of (S)-2-[1-(1,4-dimethyl-1H-indol-3-ylmethyl)-6-methoxy-2,4-dioxo-1,4-dihydro-2H-quinazolin-3-yl]-hexanoic acid methyl ester (124 mg, 0.26 mmol) in dioxane (2.5 ml) is added a solution of LiOH monohydrate (50 mg, 1.19 mmol) in H$_2$O (2.5 mL). The solution is stirred at 60° C. for 4 hours. The reaction mixture is allowed to cool to room temperature, quenched with 4M HCl in dioxane (500 μL) and concentrated. The resulting residue is triturated with H$_2$O and MeOH to afford the title compound. LCMS (ESMS): m/z 464.87 (M+H$^+$)

The following compounds are synthesized using a similar procedure.
(S)-2-[1-(4,6-Dimethyl-1,2-benzisothiazol-3-ylmethyl)-6-methoxy-2,4-dioxo-1,4-dihydro-2H-quinazolin-3-yl]-hexanoic acid. LCMS (ESMS): m/z 482.90 (M+H$^+$).
(R)-2-[1-(1,4-Dimethyl-1H-indol-3-ylmethyl)-6-methoxy-2,4-dioxo-1,4-dihydro-2H-quinazolin-3-yl]-hexanoic acid. LCMS (ESMS): m/z 464.87 (M+H$^+$)
(S)-2-[1-(1,4-Dimethyl-1H-indol-3-ylmethyl)-6,7-dimethoxy-2,4-dioxo-1,4-dihydro-2H-quinazolin-3-yl]-hexanoic acid. LCMS (ESMS): m/z 494.92 (M+H$^+$)

Example 11

1-(1,4-Dimethyl-1H-indol-3-ylmethyl)-3-(2-morpholin-4-yl-ethyl)-1H-quinazoline-2,4-dione To a mixture of isatoic anhydride (500 mg, 3.07 mmol) and 1-(4-chloro-phenyl)-ethylamine (530 mg, 3.68 mmol) in CH$_2$Cl$_2$ (20 mL) is added diisopropyl ethyl amine (1.2 mL, 6.89 mmol). The mixture is stirred at room temperature for 16 hours. The reaction mixture is diluted with EtOAc (100 mL) and is washed with H$_2$O (50 mL×3). The organic layer is dried over sodium sulfate, concentrated and the resulting residue is purified by flash chromatography with 25% EtOAc in Hexane as the eluent to afford the desired to afford the desired 2-amino-N-[1-(4-chloro-phenyl)-ethyl]-benzamide (115 mg, 14%).

To a solution of 2-amino-N-[1-(4-chloro-phenyl)-ethyl]-benzamide (115 mg, 0.42 mmol) in THF (30 mL) is added trichloromethyl chloroformate (50 mg, 0.25 mmol). The mixture is stirred at 90° C. for 4 hours. The reaction mixture is allowed to cool to room temperature, neutralizes with 1M NaOH aq. The reaction mixture is extracted with EtOAc (50 mL×3). The organic layer is dried over sodium sulfate and is concentrated to give the desired 3-[1-(4-chloro-phenyl)-ethyl]-1H-quinazoline-2,4-dione (125 mg, 99%).

To a mixture of 3-[1-(4-chloro-phenyl)-ethyl]-1H-quinazoline-2,4-dione (175 mg, 0.58 mmol) and (1,4-dimethyl-1H-indol-3-ylmethyl)-trimethylammonium iodide (210 mg, 0.61 mmol) in DMF (2.5 mL) is added K$_2$CO$_3$ (100 mg, 0.72 mmol). The mixture is stirred at 60° C. for 4 hours.

The reaction mixture is allowed to cool to room temperature, diluted with EtOAc (50 mL) and is washed with H$_2$O (50 mL×3). The organic layer is dried over sodium sulfate and is concentrated. The resulting residue is recrystallized with EtOAc and hexanes to afford the title compound. LCMS (ESMS): m/z 433.90 (M+H$^+$)

The following compounds are prepared using a similar procedure.
1-(1,4-Dimethyl-1H-indol-3-ylmethyl)-3-(2-methoxy-1-methyl-ethyl)-1H-quinazoline-2,4-dione. LCMS (ESMS): m/z 392.11 (M+H$^+$).

Example 12

(R)-2-[1-(1,4-Dimethyl-1H-indol-3-ylmethyl)-2,4-dioxo-1,4-dihydro-2H-quinazolin-3-yl]-pentanoic acid amide To the suspension of (R)-2-[1-(1,4-Dimethyl-1H-indol-3-ylmethyl)-2,4-dioxo-1,4-dihydro-2H-quinazolin-3-yl]-pentanoic acid (95 mg, 0.23 mmol), (prepared according to example 4) in THF (2.5 mL) at room temperature are added 0.5 M NH$_3$ in 1,4-dioxane solution (0.91 mL, 0.45 mmol) and HOBt (15 mg, 0.11 mmol). Then EDC (87 mg, 0.45 mmol) is added in small portions. The reaction mixture is stirred for 16 hours and then DMF (1.0 mL) along with another 0.5 M NH$_3$ (1.0 mL) in 1,4-dioxane solution and EDC (87 mg, 0.45 mmol) are added. The reaction is continued for another 60 hours. Then water (55 mL) is added and the mixture is extracted with EtOAc (3×30 mL). The organic layers are combined, dried over Na$_2$SO$_4$ and are concentrated to give crude product. Purification by flash column chromatography using 6% MeOH in DCM followed by washing using Methanol affords the title compound. LCMS (ESMS): m/z 419.77 (M+H$^+$).

Supplementary Experimental

Example A (R)-amino-cyclohexyl-acetic acid methyl ester hydrochloride

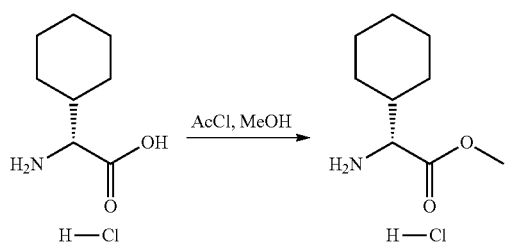

To a solution of acetyl chloride (0.5 mL, 7.04 mmol) in MeOH (10 mL) at 0° C. is added (R)-amino-cyclohexyl-acetic acid hydrochloride (1.0 g, 5.16 mmol). The mixture is stirred at 60° C. for 16 hours. The reaction mixture is allowed to cool to room temperature and concentrated. The resulting residue is triturated with $Et_2O$ to afford the title compound (1.0 g, 93%).

The following amino acid esters are prepared using a similar procedure.
(1-Amino-cyclohexyl)-acetic acid methyl ester hydrochloride
3-Amino-4-phenyl-butyric acid methyl ester hydrochloride
2-Amino-2-methyl-butyric acid methyl ester hydrochloride
(1-Aminomethyl-cyclohexyl)-acetic acid methyl ester hydrochloride
4-Amino-3-phenyl-butyric acid methyl ester hydrochloride
(R)-2-Amino-hexanoic acid methyl ester; hydrochloride Example B 2-Amino-pentanoic acid methyl ester; hydrochloride

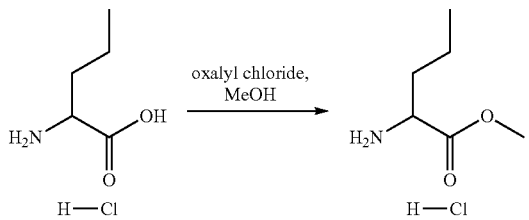

To a solution of oxalyl chloride (1.5 mL, 17.19 mmol) in MeOH (10 mL) at 0° C. is added 2-amino-pentanoic acid hydrochloride (1.0 g, 8.54 mmol). The mixture is stirred at 60° C. for 30 minutes. The reaction mixture is allowed to cool to room temperature and is concentrated. The resulting residue is triturated with $Et_2O$ to afford the title compound (1.4 g, 100%).

The following amino acid ester is prepared using a similar procedure
3-Amino-heptanoic acid methyl ester hydrochloride Example C (S)-2-amino-butyric acid methyl ester

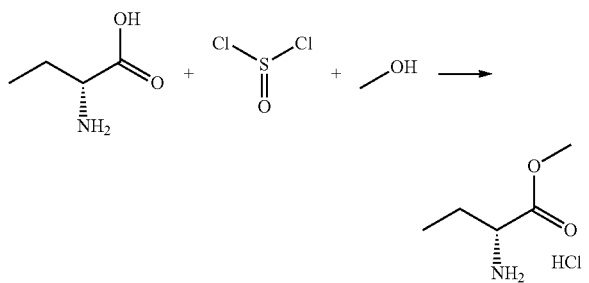

A solution of (S)-2-amino-butyric acid (1.0 g, 9.7 mmol) in methanol (20 mL) is cooled to 0° C. and thionyl chloride (1.0 mL, 13.7 mmol) is added dropwise. The reaction mixture is stirred at ambient temperature for 40 hours is then concentrated to provide the title compound (1.38 g, 93%).

Following amino acid esters are prepared using a similar procedure
2-Amino-2-methyl-propionic acid methyl ester hydrochloride
3-Amino-pentanoic acid methyl ester hydrochloride
2-Amino-butyric acid methyl ester hydrochloride
1-Amino-cyclohexanecarboxylic acid methyl ester hydrochloride Example D (S)-3-Amino-hexanoic acid ethyl ester

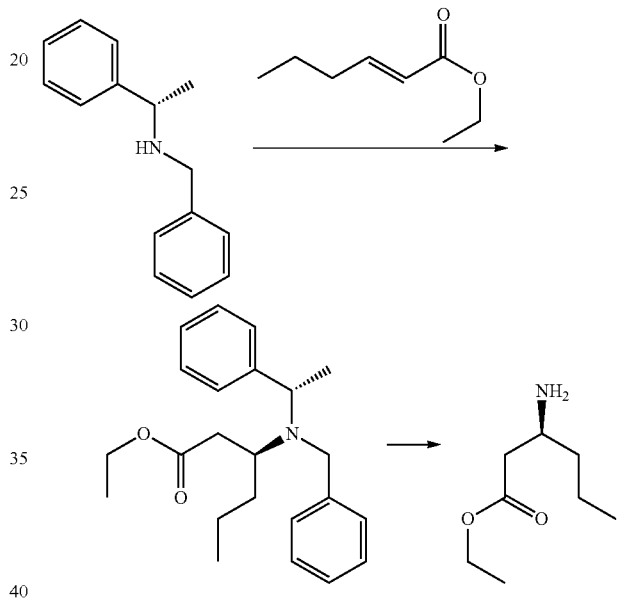

To a solution of (S)-(−)-N-benzyl-alpha-methyl-benzylamine (50 mL, 239 mmol) in THF (150 mL) at 0° C. is added nBuLi (2.5 M in THF) (100 mL, 250 mmol) under nitrogen atmosphere. The solution is cooled to −78° C. and ethyl trans-2-hexenoate (16.6 g, 117 mmol) is added. The solution is stirred for 1 hour and saturated $NH_4Cl$ solution is added. The solution is warmed to room temperature and is extracted with EtOAc. The combined organic layer is dried with $MgSO_4$ and is filtered. The filtrate is concentrated and the residue is purified by flash chromatography with 5% EtOAc in Hexane as the eluent to afford the (S)-3-[Benzyl-((S)-1-phenyl-ethyl)-amino]-hexanoic acid ethyl ester (20.8 g, 50%) as a colorless oil.

To a solution of (S)-3-[Benzyl-((S)-1-phenyl-ethyl)-amino]-hexanoic acid ethyl ester (20.8 g, 59 mmol) in EtOH (50 mL) is added $Pd(OH)_2$ (20% in carbon) (2 g). The mixture is stirred under hydrogen atmosphere with 40 psi for 16 hours. The mixture is filtered and the filtrate is concentrated to give the title compound (8.2 g, 87%).

Methods of Use

In accordance with the invention, there are provided methods of using the compounds as described herein and their pharmaceutically acceptable derivatives. The compounds used in the invention inhibit Chymase. Since Chymase is known to transform angiotensin Ito angiotensin II and may contribute to activation of TGF-β, matrix proteases and cytokines, the inhibition of Chymase is an attractive means for preventing and treating a variety of diseases or conditions. Examples include heart failure including chronic heart failure (non-ischemic), post-myocardial infarction heart failure (ischemic), acute myocardial infarction, reperfusion injury, left ventricular dysfunction, cardiac fibrosis, diastolic heart failure and hypertrophic cardiomyopathy, hypertension including pulmonary hypertension, systolic hypertension and resistant hypertenstion, including coronary artery disease, peripheral arterial occlusive disease, aneurism, stable/unstable angina, restenosis, diabetic nephropathy, atrial fibrillation/ventricular arrhythmias, valvular heart disease, pericardial diseases, renal insufficiency (chronic kidney disease, end stage renal disease), stroke. The compounds of the invention may also be useful for the following procedures: coronary artery bypass grafting, percutaneous coronary intervention and stenting.

Other diseases within the scope of the invention include allergic rhinitis, dermatitis, asthma, chronic obstructive pulmonary disease (COPD), and pulmonary inflammation, asthma, osteoarthritis, bone resorption diseases, multiple sclerosis, Guillain-Barre syndrome, Crohn's disease, ulcerative colitis, psoriasis, graft versus host disease, systemic lupus erythematosus, rheumatoid arthritis, toxic shock syndrome, Alzheimer's disease, inflammatory bowel diseases, acute and chronic pain as well as symptoms of inflammation, thermal injury, adult respiratory distress syndrome (ARDS), multiple organ injury secondary to trauma, acute glomerulonephritis, dermatoses with acute inflammatory components, acute purulent meningitis or other central nervous system disorders, syndromes associated with hemodialysis, leukopherisis, granulocyte transfusion associated syndromes, and necrotizing entrerocolitis, traumatic arthritis, and sepsis. Reference in this regard may be made to U.S. Pat. Nos. 5,948,785 ; 6,271,238; 5,691,335; 5,814,631; 6,300,337; EP 1,099,690; U.S. Pat. No. 6,323,219; US 2005-0245536 A1; Fukami, et al., *Current Pharmaceutical Design* 1998, vol. 4, pp. 439-453.

As disclosed in the Background of the Invention, the compounds of the invention may contribute to activation of cytokines, they will therefore be useful for treating oncological diseases. Reference in this regard may be made to US 2005-0245536 A1. These diseases include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma and mesothelioma.

Examples of brain cancers include, but are not limited to brain stem, optic and hypophtalmic glioma, cerebella and cerebral astrocytoma, medulloblastoma, ependymoma, as well as pituitary,neuroectodermal and pineal tumor.

Examples of peripheral nervous system tumors include, but are not limited to neuroblastoma, ganglioneuroblastoma, and peripheral nerve sheath tumors.

Examples of tumors of the endocrine and exocrine system include, but are not limited to thyroid carcinoma, adrenocortical carcinoma, pheochromocytoma, and carcinoid tumors.

Tumors of the male reproductive organs include, but are not limited to prostate and testicular cancer.

Tumors of the female reproductive organs include, but are not limited to endometrial, cervical, ovarian, vaginal.

These disorders have been well characterized in man, but also exist with a similar etiology in other mammals, and can be treated by pharmaceutical compositions of the present invention.

For therapeutic use, the compounds may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds described herein may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients.

Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Combinations with other therapeutics include but are not limited to: angiotensin II receptor blockers, angiotensin converting enzyme inhibitors, CETP inhibitors/apoA1 mimetics, adenosine diphosphate (P2Y12) inhibitors, direct thrombin inhibitors, aldosterone antagonists, factor Xa inhibitors, natriuretic peptides (ANP/BNP), renin inhibitors, anti-arrhythmics, Chymase inhibitors, HMG-CoA Reductase inhibitors (Statins), Rho kinase inhibitors, beta-blockers, Lipoprotein-associated phospholipase A2 inhibitors, cardiac glycosides, calcium channel blockers, diuretics, fibrates, Endothelin Receptor Antagonists, GPIIb/IIIa inhibitors, histone deacetylase inhibitors, heparins, nicotinic acid derivatives,vasopeptidase inhibitors, nitrites and nitrates, fatty acid oxidation inhibitors, oral anticoagulants, acyl-CoA:cholesterol acyltransferase inhibitors, thrombolytics, microsomal triglyceride transfer protein inhibitors, thiazolidinediones, adenosine receptor modulators, cholesterol absorbtion inhibitors, Advanced Glycation End products/receptor (AGE/RAGE) interaction modulators/blockers, acetyl salicylic acid, dipyridamole, gene therapy and cell therapy.

Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the above-described compounds include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

The term "patient" includes both human and non-human mammals.

The term "effective amount" means an amount of a compound according to the invention which, in the context of which it is administered or used, is sufficient to achieve the desired effect or result. Depending on the context, the term effective amount may include or be synonymous with a pharmaceutically effective amount or a diagnostically effective amount.

The terms "pharmaceutically effective amount" or "therapeutically effective amount" means an amount of a compound according to the invention which, when administered to a patient in need thereof, is sufficient to effect treatment for disease-states, conditions, or disorders for which the compounds have utility. Such an amount would be sufficient to elicit the biological or medical response of a tissue, system, or patient that is sought by a researcher or clinician. The amount of a compound of according to the invention which constitutes a therapeutically effective amount will vary depending on such factors as the compound and its biological activity, the composition used for administration, the time of administration, the route of administration, the rate of excretion of the compound, the duration of treatment, the type of disease-state or disorder being treated and its severity, drugs used in combination with or coincidentally with the compounds of the invention, and the age, body weight, general health, sex, and diet of the patient. Such a therapeutically effective amount can be determined routinely by one of ordinary skill in the art having regard to their own knowledge, the prior art, and this disclosure.

The term "diagnostically effective amount" means an amount of a compound according to the invention which, when used in a diagnostic method, apparatus, or assay, is sufficient to achieve the desired diagnostic effect or the desired biological activity necessary for the diagnostic method, apparatus, or assay. Such an amount would be sufficient to elicit the biological or medical response in a diagnostic method, apparatus, or assay, which may include a biological or medical response in a patient or in a in vitro or in vivo tissue or system, that is sought by a researcher or clinician. The amount of a compound according to the invention which constitutes a diagnostically effective amount will vary depending on such factors as the compound and its biological activity, the diagnostic method, apparatus, or assay used, the composition used for administration, the time of administration, the route of administration, the rate of excretion of the compound, the duration of administration, drugs and other compounds used in combination with or coincidentally with the compounds of the invention, and, if a patient is the subject of the diagnostic administration, the age, body weight, general health, sex, and diet of the patient. Such a diagnostically effective amount can be determined routinely by one of ordinary skill in the art having regard to their own knowledge, the prior art, and this disclosure.

The terms "treating" or "treatment" mean the treatment of a disease-state in a patient, and include:

(i) preventing the disease-state from occurring in a patient, in particular, when such patient is genetically or otherwise predisposed to the disease-state but has not yet been diagnosed as having it;

(ii) inhibiting or ameliorating the disease-state in a patient, i.e., arresting or slowing its development; or (iii) relieving the disease-state in a patient, i.e., causing regression or cure of the disease-state.

In vitro Assay for Inhibition of Chymase

Chymase assays were performed in a total volume of 15 µL in Corning black opaque 384-well microtiter plates with a non-binding surface (Coming, N.Y.). The assay buffer was comprised of 20 mM Tris HCl pH 8.0, 50 mM NaCl, 0.01% CHAPS. The test compounds were serially diluted 3-fold with neat DMSO in a 96-well polypropylene plate from a 10 mM DMSO stock to give the 10 point dose response curve. 3 µL of the resulting DMSO solution were transferred to a 384-well polypropylene plate in duplicate, and 37 µL of assay buffer was added. Chymase was added to the assay plate in 3 uL of assay buffer followed by 2 uL of the appropriate compound dilution using a PlateMate Plus (Matrix Technologies Corp., Hudson, N.H.). The reaction was initiated by the addition of 10 uL rhodamine 110, bis-(succinoyl-L-alanyl-L-alanyl-L-prolyl-L-phenylalanylamide) (American Peptides, Sunnyvale, Calif.) in assay buffer containing 150 µM tris(2-carboxyethyl)phosphine (TCEP, Pierce Chemical, Rockford, Ill.) using a Multidrop (Thermo Electron Corp., Waltham, Mass.). Final assay concentrations were 500 pM chymase, 100 nM substrate, 100 µM TCEP, and 1% DMSO. The plates were incubated at 28° C. and 80% humidity for 1 hour, at which time the fluorescence was read on a Viewlux 1430 Microplate Imager (Perkin Elmer Life Sciences, Boston, Mass.) with 485 nm excitation, 530 nm emission, and a fluorescein dichroic mirror. The percentage of control values were calculated relative to assay blanks containing complete reaction minus chymase and a 100% control containing assay buffer with 1% DMSO in place of compound. IC50 values were obtained by fitting the data using XLFit4 (IDBS Software).

Preferred compounds of the invention have an IC50 activity of 10 nanoMolar (nM) or less.

All patent and literature references cited in this application are incorporated herein by reference in their entirety.

The invention claimed is:

1. A compound of the formula (I):

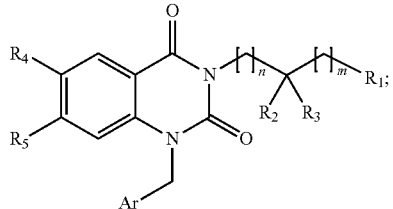

wherein m and n are each independently 0-2;

$R_1$ is halogen, trihalomethyl, cyano, amino, hydroxyl, C1-4 alkyl, C1-4 alkoxyl, $COR_6$, $COOR_6$, $CONR_6R_7$, $NR_6R_7$;

$R_2$ and $R_3$ are each independently hydrogen, halogen, trihalomethyl, cyano, amino, hydroxyl, C1-4 alkyl, carbocycle optionally substituted by halogen or C1-4 alkyl, C1-4 alkoxy, $COR_6$, $COOR_6$, $CONR_6R_7$ or $NR_6R_7$, wherein $R_2$ and $R_3$ cannot simultaneously be hydrogen;

or $R_2$ and $R_3$ optionally together cyclize to the C atom to which they are attached to form a carbocyclic or heterocyclic ring optionally substituted by one or more halogen or C1-4 alkyl, C1-4 alkoxyl, trihalomethyl, cyano, amino, hydroxyl, $COR_6$, $COOR_6$, $CONR_6R_7$ or $NR_6R_7$;

$R_4$ and $R_5$ are each independently hydrogen, trihalomethyl, cyano, amino, hydroxyl, C1-4 alkyl, methoxy, $COR_6$, $COOR_6$, $CONR_6R_7$ or $NR_6R_7$;

Ar is a mono- or poly-substituted or unsubstituted fused heteroaromatic group having 7-10 carbon atoms and containing one or more hetero atoms selected from the group consisting of an oxygen atom, a nitrogen atom and a sulfur atom in its ring(s); each substituent on said aromatic or heteroaromatic groups is selected from a halogen, hydroxyl, nitro, cyano, a linear or branched C1-6 alkyl group, a linear or branched C1-6 alkoxy (including the case in which two adjacent groups form an acetal bond), a linear or branched C1-6 alkylthio, a linear or branched C1-6 alkylsulfonyl group, phenylsulfonyl, a linear or branched C1-6 acyl group, a linear or branched C1-6 acylamino, trihalomethyl, trihalomethoxy, phenyl, $COOR_6$, $CONR_6R_7$, $SO_2NR_6R_7$, $NR_6R_7$ and phenoxy group that may be substituted by one or more halogen atoms;

$R_6$, $R_7$ each independently represent a hydrogen atom or linear or branched alkyl group having 1-6 carbon atoms, or $R_6$ and $R_7$ optionally together represent —$CH_2$—$CH_2$—, —$CH_2$—$CH_2$—$CH_2$— or —$CH_2$—$CH_2$—$CH_2$ and cyclize to the N atom to which they are attached to form a heterocycle ring optionally substituted by one or more C1-4 alkyl;

with the proviso that Ar is not an optionally substituted benzimidazolyl ring;

or a pharmaceutically acceptable salt thereof.

2. The compound according to claim 1 wherein:

Ar is indolyl, azaindolyl, isoindolyl, benzoxazolyl, benzothiazolyl, benzisothiazolyl, isoquinolinyl, quinolinyl, benzofuranyl, benzodioxolyl or indazolyl each optionally substituted with a group selected from a halogen, hydroxyl, nitro, cyano, a linear or branched C1-6 alkyl group, a linear or branched C1-6 alkoxy (including the case in which two adjacent groups form an acetal bond), a linear or branched C1-6 alkylthio, a linear or branched C1-6 alkylsulfonyl group, phenylsulfonyl, a linear or branched C1-6 acyl group, a linear or branched C1-6 acylamino, trihalomethyl, trihalomethoxy, phenyl, $COOR_6$, $CONR_6R_7$, $SO_2NR_6R_7$, $NR_6R_7$ and phenoxy group that may be substituted by one or more halogen atoms;

$R_1$ is C1-4 alkoxyl, $COR_6$, $COOR_6$ or $CONR_6R_7$;

$R_2$ and $R_3$ are each independently hydrogen, C1-4 alkyl, C3-6 cycloalkyl or phenyl each ring is optionally substituted by halogen or C1-4 alkyl, wherein $R_2$ and $R_3$ cannot simultaneously be hydrogen;

or $R_2$ and $R_3$ optionally together cyclize to the C atom to which they are attached to form a C3-6 cycloalkyl or C3-6 heterocyclic ring optionally substituted by one or more halogen or C1-4 alkyl;

$R_4$ and $R_5$ are each independently hydrogen, C1-4 alkyl or methoxy.

3. The compound according to claim 2 wherein:

Ar is indolyl or benzisothiazolyl each optionally substituted with a group selected from a halogen, hydroxyl, nitro, cyano, a linear or branched C1-6 alkyl group, a linear or branched C1-6 alkoxy, a linear or branched C1-6 alkylthio, a linear or branched C1-6 alkylsulfonyl group, a linear or branched C1-6 acyl group, a linear or branched C1-6 acylamino, trihalomethy and trihalomethoxy;

$R_1$ is $COR_6$, $COOR_6$ or $CONR_6R_7$;

$R_2$ and $R_3$ are each independently hydrogen, methyl, ethyl, propyl, butyl, cyclopropyl, cyclohexyl or phenyl each ring is optionally substituted by halogen or C1-4 alkyl, wherein $R_2$ and $R_3$ cannot simultaneously be hydrogen;

or $R_2$ and $R_3$ optionally together cyclize to the C atom to which they are attached to form cyclohexyl, tetrahydropyranyl, optionally substituted by one or more halogen or C1-4 alkyl.

4. The compound according to claim 3 wherein:

Ar is indolyl or benzisothiazolyl each optionally substituted with a linear or branched C1-6 alkyl group.

5. The compound according to claim 4 wherein:

Ar is

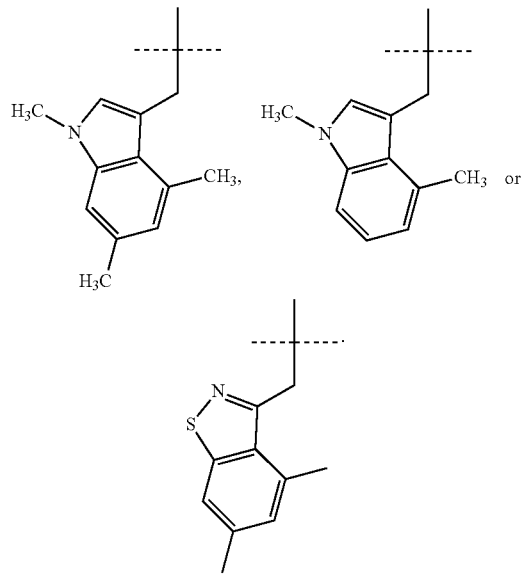

6. A compound chosen from (S)-2-[1-(1,4-Dimethyl-1H-indol-3-ylmethyl)-2,4-dioxo-1,4-dihydro-2H-quinazolin-3-yl]-pentanoic acid;
(R)-2-[1-(1,4-Dimethyl-1H-indol-3-ylmethyl)-2,4-dioxo-1,4-dihydro-2H-quinazolin-3-yl]-hexanoic acid;
(S)-2-[1-(1,4-Dimethyl-1H-indol-3-ylmethyl)-7-methoxy-2,4-dioxo-1,4-dihydro-2H-quinazolin-3-yl]-hexanoic acid;
(R)-3-[1-(1,4-Dimethyl-1H-indol-3-ylmethyl)-2,4-dioxo-1,4-dihydro-2H-quinazolin-3-yl]-3-phenyl-propionic acid;
(R)-[1-(1,4-Dimethyl-1H-indol-3-ylmethyl)-2,4-dioxo-1,4-dihydro-2H-quinazolin-3-yl]-phenyl-acetic acid;
(S)-3-[1-(4,6-Dimethyl-l,2-benzisothiazol-3-ylmethyl)-2,4-dioxo-1,4-dihydro-2H-quinazolin-3-yl]-pentanoic acid;
(R)-2-[1-(1,4-Dimethyl-1H-indol-3-ylmethyl)-2,4-dioxo-1,4-dihydro-2H-quinazolin-3-yl]-butyric acid;
(R)-2-[2,4-Dioxo-1-(1,4,6-trimethyl-1H-indol-3-ylmethyl)-1,4-dihydro-2H-quinazolin-3-yl]-pentanoic acid;
(R)-2-[1-(1,4-Dimethyl-1H-indol-3-ylmethyl)-6-methoxy-2,4-dioxo-1,4-dihydro-2H-quinazolin-3-yl]-hexanoic acid;
3-[1-(1,4-Dimethyl-1H-indol-3-ylmethyl)-2,4-dioxo-1,4-dihydro-2H-quinazolin-3-yl]-heptanoic acid;
(R)-[1-(4,6-Dimethyl-1,2-benzisothiazol-3-ylmethyl)-2,4-dioxo-1,4-dihydro-2H-quinazolin-3-yl]-phenyl-acetic acid;
2-[1-(1,4-Dimethyl-1H-indol-3-ylmethyl)-2,4-dioxo-1,4-dihydro-2H-quinazolin-3-yl]-hexanoic acid;
{1-[1-(1,4-Dimethyl-1H-indol-3-ylmethyl)-2,4-dioxo-1,4-dihydro-2H-quinazolin-3-yl]-cyclohexyl)-acetic acid;
3-[1-(4,6-Dimethyl-1,2-benzisothiazol-3-ylmethyl)-2,4-dioxo-1,4-dihydro-2H-quinazolin-3-yl]-pentanoic acid;
(S)-2-[1-(1,4-Dimethyl-1H-indol-3-ylmethyl)-2,4-dioxo-1,4-dihydro-2H-quinazolin-3-yl]-hexanoic acid;
2-[1-(1,4-Dimethyl-1H-indol-3-ylmethyl)-2,4-dioxo-1,4-dihydro-2H-quinazolin-3-yl]-pentanoic acid;
{1-[1-(4,6-Dimethyl-1,2-benzisothiazol-3-ylmethyl)-2,4-dioxo-1,4-dihydro-2H-quinazolin-3-yl]-cyclohexyl}-acetic acid;
{1-[1-(1,4-Dimethyl-1H-indol-3-ylmethyl)-2,4-dioxo-1,4-dihydro-2H-quinazolin-3-ylmethyl-cyclohexyl}-acetic acid;
(S)-2-[1-(1,4-Dimethyl-1H-indol-3-ylmethyl)-2,4-dioxo-1,4-dihydro-2H-quinazolin-3-yl]-propionic acid;
(S)-2-[1-(1,4-Dimethyl-1H-indol-3-ylmethyl)-6-methoxy-2,4-dioxo-1,4-dihydro-2H-quinazolin-3-yl]-hexanoic acid;
4-[1-(1,4-Dimethyl-1H-indol-3-ylmethyl)-2,4-dioxo-1,4-dihydro-2H-quinazolin-3-yl]-3-phenyl-butyric acid;
(R)-2-[1-(1,4-Dimethyl-1H-indol-3-ylmethyl)-2,4-dioxo-1,4-dihydro-2H-quinazolin-3-yl]-hexanoic acid;
(R)-2-[1-(4,6-Dimethyl-1,2-benzisothiazol-3-ylmethyl)-2,4-dioxo-1,4-dihydro-2H-quinazolin-3-yl]-hexanoic acid;
1-[1-(1,4-Dimethyl-1H-indol-3-ylmethyl)-2,4-dioxo-1,4-dihydro-2H-quinazolin-3-ylmethyl]-cyclohexanecarboxylic acid;
(S)-3-[1-(1,4-Dimethyl-1H-indol-3-ylmethyl)-2,4-dioxo-1,4-dihydro-2H-quinazolin-3-yl]-pentanoic acid;
(S)-[1-(4,6-Dimethyl-1,2-benzisothiazol-3-ylmethyl)-2,4-dioxo-1,4-dihydro-2H-quinazolin-3-yl]-phenyl-acetic acid;
(R)-3-[1-(1,4-Dimethyl-1H-indol-3-ylmethyl)-2,4-dioxo-1,4-dihydro-2H-quinazolin-3-yl]-pentanoic acid;
2-[1-(1,4-Dimethyl-1H-indol-3-ylmethyl)-2,4-dioxo-1,4-dihydro-2H-quinazolin-3-yl]-butyric acid;
(S)-2-[1-(1,4-Dimethyl-1H-indol-3-ylmethyl)-2,4-dioxo-1,4-dihydro-2H-quinazolin-3-yl]-butyric acid;
(S)-2-[1-(4,6-Dimethyl-1,2-benzisothiazol-3-ylmethyl)-6-methoxy-2,4-dioxo-1,4-dihydro-2H-quinazolin-3-yl]-hexanoic acid;
(R)-2-[1-(1,4-Dimethyl-1H-indol-3-ylmethyl)-2,4-dioxo-1,4-dihydro-2H-quinazolin-3-yl]-propionic acid;
(S)-[1-(1,4-Dimethyl-1H-indol-3-ylmethyl)-2,4-dioxo-1,4-dihydro-2H-quinazolin-3-yl]-phenyl-acetic acid;
(S)-(4-Chloro-phenyl)-[1-(4,6-dimethyl-1,2-benzisothiazol-3-ylmethyl)-2,4-dioxo-1,4-dihydro-2H-quinazolin-3-yl]-acetic acid;
3-[1-(1,4-Dimethyl-1H-indol-3-ylmethyl)-dioxo-1,4-dihydro-2H-quinazolin-3-yl]-pentanoic acid;
1-[1-(1,4-Dimethyl-1H-indol-3-ylmethyl)-2,4-dioxo-1,4-dihydro-2H-quinazolin-3-yl]-cyclohexanecarboxylic acid;
(S)-2-[1-(4,6-Dimethyl-1,2-benzisothiazol-3-ylmethyl)-2,4-dioxo-1,4-dihydro-2H-quinazolin-3-yl]-propionic acid;
(S)-3-[1-(1,4-Dimethyl-1H-indol-3-ylmethyl)-2,4-dioxo-1,4-dihydro-2H-quinazolin-3-yl]-hexanoic acid;
(S)-3-[1-(1,4-Dimethyl-1H-indol-3-ylmethyl)-2,4-dioxo-1,4-dihydro-2H-quinazolin-3-yl]-3-phenyl-propionic acid;
(S)-2-[1-(4,6-Dimethyl-1,2-benzisothiazol-3-ylmethyl)-2,4-dioxo-1,4-dihydro-2H-quinazolin-3-yl]-hexanoic acid;

(R)-2-[1-(4,6-Dimethyl-1,2-benzisothiazol-3-ylmethyl)-2,4-dioxo-1,4-dihydro-2H-quinazolin-3-yl]-butyric acid;
(R)-2-[1-(4,6-Dimethyl-1,2-benzisothiazol-3-ylmethyl)-2,4-dioxo-1,4-dihydro-2H-quinazolin-3-yl]-propionic acid;
3-[1-(1,4-Dimethyl-1H-indol-3-ylmethyl)-2,4-dioxo-1,4-dihydro-2H-quinazolin-3-yl]-butyric acid;
(R)-3-[1-(4,6-Dimethyl-benzo[d]isothiazol-3-ylmethyl)-2,4-dioxo-1,4-dihydro-2H-quinazolin-3-yl]-pentanoic acid;
(R)-Cyclohexyl-[1-(1,4-dimethyl-1H-indol-3-ylmethyl)-2,4-dioxo-1,4-dihydro-2H-quinazolin-3-yl]-acetic acid;
(S)-Cyclohexyl-[1-(1,4-dimethyl-1H-indol-3-ylmethyl)-2,4-dioxo-1,4-dihydro-2H-quinazolin-3-yl]-acetic acid;
(S)-2-[1-(1,4-Dimethyl-1H-indol-3-ylmethyl)-6,7-dimethoxy-2,4-dioxo-1,4-dihydro-2H-quinazolin-3-yl]-hexanoic acid;
2-[1-(1,4-Dimethyl-1H-indol-3-ylmethyl)-2,4-dioxo-1,4-dihydro-2H-quinazolin-3-yl]-2-methyl-butyric acid;
{4-[1-(1,4-Dimethyl-1H-indol-3-ylmethyl)-2,4-dioxo-1,4-dihydro-2H-quinazolin-3-yl]-tetrahydro-pyran-4-yl}-acetic acid;
2-[1-(1,4-Dimethyl-1H-indol-3-ylmethyl)-2,4-dioxo-1,4-dihydro-2H-quinazolin-3-yl]-2-methyl-propionic acid;
(R)-2-[1-(1,4-Dimethyl-1H-indol-3-ylmethyl)-2,4-dioxo-1,4-dihydro-2H-quinazolin-3-yl]-pentanoic acid amide;
(R)-2-[1-(1,4-Dimethyl-1H-indol-3-ylmethyl)-2,4-dioxo-1,4-dihydro-2H-quinazolin-3-yl]-propionic acid methyl ester;
(S)-2-[1-(1,4-Dimethyl-1H-indol-3-ylmethyl)-2,4-dioxo-1,4-dihydro-2H-quinazolin-3-yl]-propionic acid methyl ester;
(R)-2-[1-(4,6-Dimethyl-1,2-benzisothiazol-3-ylmethyl)-2,4-dioxo-1,4-dihydro-2H-quinazolin-3-yl]-propionic acid methyl ester;
1-(1,4-Dimethyl-1H-indol-3-ylmethyl)-3-(2-methoxy-1-methyl-ethyl)-1H-quinazoline-2,4-dione;
(S)-2-[1-(1,4-Dimethyl-1H-indol-3-ylmethyl)-2,4-dioxo-1,4-dihydro-2H-quinazolin-3-yl]-butyric acid methyl ester;
(S)-2-[1-(4,6-Dimethyl-1,2-benzisothiazol-3-ylmethyl)-2,4-dioxo-1,4-dihydro-2H-quinazolin-3-yl]-propionic acid methyl ester;
(R)-2-[1-(1,4-Dimethyl-1H-indol-3-ylmethyl)-2,4-dioxo-1,4-dihydro-2H-quinazolin-3-yl]-butyric acid methyl ester;
1-(1,4-Dimethyl-1H-indol-3-ylmethyl)-3-propyl-1H-quinazoline-2,4-dione
(S)-2-[1-(4,6-Dimethyl-1,2-benzisothiazol-3-ylmethyl)-2,4-dioxo-1,4-dihydro-2H-quinazolin-3-yl]-butyric acid;
(R)-(4-Chloro-phenyl)-[1-(4,6-dimethyl-1,2-benzisothiazol-3-ylmethyl)-2,4-dioxo-1,4-dihydro-2H-quinazolin-3-yl]-acetic acid;
(R)-2-[1-(4,6-Dimethyl-1,2-benzisothiazol-3-ylmethyl)-2,4-dioxo-1,4-dihydro-2H-quinazolin-3-yl]-butyric acid methyl ester;
(S)-2-[1-(4,6-Dimethyl-1,2-benzisothiazol-3-ylmethyl)-2,4-dioxo-1,4-dihydro-2H-quinazolin-3-yl]-butyric acid methyl ester;
3-Cyclopropyl-3-[1-(1,4-dimethyl-1H-indol-3-ylmethyl)-2,4-dioxo-1,4-dihydro-2H-quinazolin-3-yl]-propionic acid;
3-Cyclopropyl-3-[1-(4,6-dimethyl-1,2-benzisothiazol-3-ylmethyl)-2,4-dioxo-1,4-dihydro-2H-quinazolin-3-yl]-propionic acid;
(R)-Cyclopropyl-[1-(1,4-dimethyl-1H-indol-3-ylmethyl)-2,4-dioxo-1,4-dihydro-2H-quinazolin-3-yl]-acetic acid;
(S)-Cyclopropyl-[1-(4,6-dimethyl-1,2-benzisothiazol-3-ylmethyl)-2,4-dioxo-1,4-dihydro-2H-quinazolin-3-yl]-acetic acid;
(R)-Cyclopropyl-[1-(4,6-dimethyl-1,2-benzisothiazol-3-ylmethyl)-2,4-dioxo-1,4-dihydro-2H-quinazolin-3-yl]-acetic acid;
(S)-Cyclopropyl-[1-(1,4-dimethyl-1H-indol-3-ylmethyl)-2,4-dioxo-1,4-dihydro-2H-quinazolin-3-yl]-acetic acid;
3-[1-(4-Chloro-phenyl)-ethyl]-1-(1,4-dimethyl-1H-indol-3-ylmethyl)-1H-quinazoline-2,4-dione; and
(R)-2-[2,4-Dioxo-1-(1,4,6-trimethyl-1H-indol-3-ylmethyl)-1,4-dihydro-2H-quinazolin-3-yl]-hexanoic acid or a pharmaceutically acceptable salt thereof.

7. A pharmaceutical composition comprising a therapeutically effective amount of a compound according to claim 1 and one or more pharmaceutically acceptable carries and or adjuvants.

* * * * *